(12) United States Patent
Wiedmann et al.

(10) Patent No.: US 11,860,319 B2
(45) Date of Patent: Jan. 2, 2024

(54) HIGH-RESOLUTION DETECTOR HAVING A REDUCED NUMBER OF PIXELS

(71) Applicant: GE Precision Healthcare LLC, Wauwatosa, WI (US)

(72) Inventors: Uwe Wiedmann, Clifton Park, NY (US); Biju Jacob, Niskayuna, NY (US); Brian David Yanoff, Schenectady, NY (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 0 days.

(21) Appl. No.: 17/691,248

(22) Filed: Mar. 10, 2022

(65) Prior Publication Data

US 2023/0288580 A1 Sep. 14, 2023

(51) Int. Cl.
  *G01T 1/17* (2006.01)
  *A61B 6/00* (2006.01)
  *G01T 1/24* (2006.01)

(52) U.S. Cl.
  CPC .............. *G01T 1/17* (2013.01); *A61B 6/4241* (2013.01); *A61B 6/484* (2013.01); *G01T 1/247* (2013.01)

(58) Field of Classification Search
  CPC ......... A61B 6/4241; A61B 6/484; G01T 1/17; G01T 1/247
  See application file for complete search history.

(56) References Cited

U.S. PATENT DOCUMENTS

| | | |
|---|---|---|
| 5,812,690 A | 9/1998 | Fordham |
| 8,405,038 B2 | 3/2013 | Bouhnik et al. |
| 8,586,937 B2 | 11/2013 | Bouhnik et al. |
| 11,054,371 B2 | 7/2021 | Danielsson |
| 2009/0110144 A1* | 4/2009 | Takahashi ............. G01T 1/2928 378/62 |
| 2010/0220832 A1* | 9/2010 | Ning .................... A61B 6/4291 378/4 |
| 2010/0246765 A1* | 9/2010 | Murakoshi ........... G01N 23/041 378/62 |
| 2010/0272235 A1* | 10/2010 | Takahashi ............. A61B 6/4291 378/62 |

(Continued)

OTHER PUBLICATIONS

Viermetz, Manuel, et al.; "Dark-field computed tomography reaches the human scale", PNAS 2022, vol. 119, No. 8; pp. 1-8.

*Primary Examiner* — Blake C Riddick
(74) *Attorney, Agent, or Firm* — Fletcher Yoder P.C.

(57) ABSTRACT

A phase-contrast imaging detector includes a plurality of pixels. Each pixel includes a detection material that generates a measurable parameter in response to X-ray photons. Each pixel also includes a plurality of sub-pixel resolution readout structures. The sub-pixel resolution readout structures are in an alternating pattern with a spacing therebetween that is larger than a frequency of a phase-contrast interference pattern but small enough to enable charge sharing between adjacent sub-pixel resolution readout structures when an X-ray photon hits between the adjacent sub-pixel resolution readout structures. The phase-contrast imaging detector also includes readout circuitry configured to read out signals from the plurality of sub-pixel readout structures. The plurality of sub-pixel resolution readout structures includes two or more electrodes having alternating arms that form an interleaved comb structure.

14 Claims, 18 Drawing Sheets

(56) References Cited

U.S. PATENT DOCUMENTS

| | | | | |
|---|---|---|---|---|
| 2012/0140883 A1* | 6/2012 | Iwakiri | ............... | A61B 6/4291 |
| | | | | 378/62 |
| 2012/0153177 A1* | 6/2012 | Iwakiri | ............... | A61B 6/4291 |
| | | | | 250/394 |
| 2012/0163554 A1* | 6/2012 | Tada | ................... | A61B 6/4035 |
| | | | | 378/154 |
| 2012/0326049 A1* | 12/2012 | Hannemann | ........... | G01T 1/243 |
| | | | | 250/394 |
| 2014/0226783 A1* | 8/2014 | Ning | ..................... | A61B 6/502 |
| | | | | 378/19 |
| 2015/0085970 A1* | 3/2015 | Bouhnik | ............... | A61B 6/482 |
| | | | | 378/19 |
| 2015/0276939 A1* | 10/2015 | Chappo | .................. | G01T 1/161 |
| | | | | 250/361 R |
| 2017/0156686 A1* | 6/2017 | Koehler | ............... | A61B 6/4291 |
| 2017/0261442 A1* | 9/2017 | Yun | ........................ | A61B 6/484 |
| 2017/0285188 A1* | 10/2017 | Rui | .......................... | G01T 1/17 |
| 2017/0303867 A1* | 10/2017 | Roessl | ................... | A61B 6/484 |
| 2018/0188190 A1* | 7/2018 | Durko | ................... | G01N 23/041 |
| 2018/0192980 A1* | 7/2018 | Wang | ................... | A61B 6/4291 |
| 2018/0246046 A1* | 8/2018 | Kagias | ................... | A61B 6/484 |
| 2018/0259657 A1* | 9/2018 | Fu | ........................... | G01T 7/005 |
| 2019/0219713 A1* | 7/2019 | Steadman Booker | ...................... | |
| | | | | G01N 23/041 |
| 2020/0158895 A1 | 5/2020 | Danielsson et al. | | |
| 2021/0244373 A1 | 8/2021 | Wiedmann et al. | | |

\* cited by examiner

HIGH-RESOLUTION DETECTOR HAVING A REDUCED NUMBER OF PIXELS

BACKGROUND

The subject matter disclosed herein relates to X-ray imaging and, more particularly, to X-ray detectors having a reduced number of pixels.

Non-invasive imaging technologies allow images of the internal structures or features of a patient to be obtained without performing an invasive procedure on the patient. In particular, such non-invasive imaging technologies rely on various physical principles (such as the differential transmission of X-rays through a target volume, the reflection of acoustic waves within the volume, the paramagnetic properties of different tissues and materials within the volume, the breakdown of targeted radionuclides within the body, and so forth) to acquire data and to construct images or otherwise represent the observed internal features of the patient.

In many implementations of X-ray imaging detectors, the energy required for detector readout scales linearly with the number of detector pixels or detector elements. In medical imaging, the total amount of energy can be become a major limitation to detector size and detector resolution.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible forms of the subject matter. Indeed, the subject matter may encompass a variety of forms that may be similar to or different from the embodiments set forth below.

In one embodiment, a phase-contrast imaging detector is provided. The phase-contrast imaging detector includes a plurality of pixels. Each pixel includes a detection material that generates a measurable parameter in response to X-ray photons. Each pixel also includes a plurality of sub-pixel resolution readout structures. The sub-pixel resolution readout structures are in an alternating pattern with a spacing therebetween that is larger than a frequency of a phase-contrast interference pattern but small enough to enable charge sharing between adjacent sub-pixel resolution readout structures when an X-ray photon hits between the adjacent sub-pixel resolution readout structures. The phase-contrast imaging detector also includes readout circuitry configured to read out signals from the plurality of sub-pixel readout structures. The plurality of sub-pixel resolution readout structures includes two or more electrodes having alternating arms that form an interleaved comb structure.

In another embodiment, an imaging detector is provided. The phase-contrast imaging detector includes a plurality of pixels. Each pixel includes a detection material that generates a measurable parameter in response to X-ray photons. Each pixel also includes a plurality of sub-pixel resolution readout structures. The sub-pixel resolution readout structures are in an alternating pattern with a spacing therebetween that is larger than a frequency of a phase-contrast interference pattern but small enough to enable charge sharing between adjacent sub-pixel resolution readout structures when an X-ray photon hits between the adjacent sub-pixel resolution readout structures. The phase-contrast imaging detector also includes readout circuitry configured to read out signals from the plurality of sub-pixel readout structures. The plurality of sub-pixel resolution readout structures includes two or more electrodes having alternating arms that form an interleaved comb structure. Each electrode of the two or more electrodes is shaped so that adjacent electrodes form an interlocked triangular pattern between themselves to enable charge sharing. The adjacent electrodes overlap in a direction parallel to a path of the X-ray photons. Each electrode includes a first segment physically separate from a second segment in a co-linear arrangement along the direction, the second segment being configured to enable accurate measurement of the X-ray photons in the presence of an X-ray photon flux that saturates the first segment.

In a further embodiment, a photon-counting detector is provided. The photon-counting detector includes a semiconductor substrate. The photon-counting detector also includes a plurality of electrode pixels disposed on one surface of the semiconductor substrate. Each electrode pixel of the plurality of electrode pixels includes at least three electrodes that are configured to share a charge between them to enable determining both an overall charge of an electron charge cloud generated from an incident X-ray photon on the photon-counting detector and a location in both a first direction and a second direction of the electron charge cloud, the first direction being orthogonal to the second direction. The structural components of each of the at least three electrodes are smaller than a size of the electron charge cloud.

In yet a further embodiment, a photon-counting detector is provided. The photon-counting detector includes a semiconductor substrate. The photon-counting detector also includes a plurality of electrode pixels disposed on one surface of the semiconductor substrate, wherein each electrode pixel of the plurality of electrode pixels is shaped so that adjacent electrode pixels form an interlocked triangular pattern between themselves to enable charge sharing, and wherein the adjacent electrode pixels overlap in a direction parallel to a path of the X-ray photons, and wherein each electrode pixel of the plurality electrode pixels includes a first segment physically separate from a second segment in a co-linear arrangement along the direction, the second segment being configured to enable accurate measurement of the X-ray photons in the presence of an X-ray photon flux that saturates the first segment.

BRIEF DESCRIPTION OF THE DRAWINGS

These and other features, aspects, and advantages of the present subject matter will become better understood when the following detailed description is read with reference to the accompanying drawings in which like characters represent like parts throughout the drawings, wherein.

DETAILED DESCRIPTION

Figure 1:
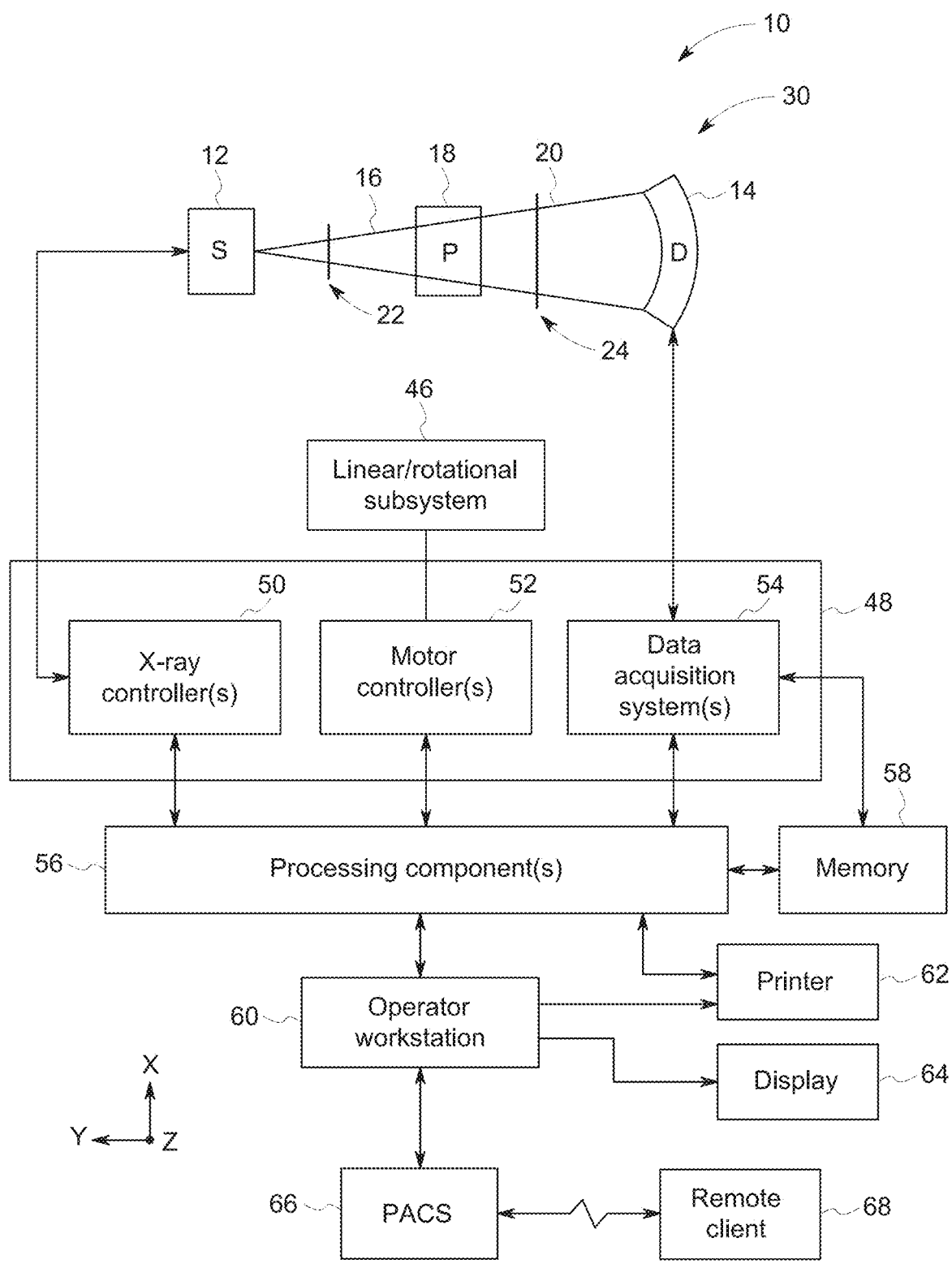
FIG. 1 is a diagrammatical view of an imaging system for use in producing images, in accordance with aspects of the present disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While aspects of the following discussion may be provided in the context of medical imaging, it should be appreciated that the present techniques are not limited to such medical contexts. Indeed, the provision of examples and explanations in such a medical context is only to facilitate explanation by providing instances of real-world implementations and applications. However, the present approaches may also be utilized in other contexts, such as tomographic image reconstruction for industrial Computed Tomography (CT) used in non-destructive inspection of manufactured parts or goods (i.e., quality control or quality review applications), and/or the non-invasive inspection of packages, boxes, luggage, and so forth (i.e., security or screening applications). In general, the present approaches may be useful in any imaging or screening context to reduce the energy required for readout by reducing the number of pixels in a detector, while maintaining or improving spatial resolution.

The present disclosure provides techniques for to reduce the energy required for readout by reducing the number of pixels in an X-ray detector, while maintaining or improving spatial resolution. In particular, in photon-counting detectors, in order to have fewer pixels but enable high resolution, a variety of controlled charge sharing techniques are utilized that enable a linear transfer function between the location of the event and an amount of charge detected in each pixel while overcoming higher count rates generated by the utilization of larger pixels. For example, in a phase-contrast detector, readout structures (e.g., electrodes) having a comb pattern are grouped together so that multiple minima/maxima correspond to a single read-out channel. In certain embodiments, the electrodes may form an interlocked triangular pattern, with each electrode having a first segment physically separate from a second segment in a co-linear arrangement. The second segment enables accurate measurement of the X-ray photons in the presence of an X-ray photon flux than saturates the first segment. In another example, in a photon-counting detector, a two-dimensional pixel structure may be utilized that includes electrode pixels (e.g., anode pixels) that include at least three electrodes. The at least three electrodes are configured to share a charge between them to enable determining both an overall charge of an electron charge cloud generated from an incident X-ray photon on the photon-counting detector and a location in both a first direction and a second direction of the electron charge cloud, the first direction being orthogonal to the second direction, and wherein structural components of each of the at least three electrodes are smaller than a size of the electron charge cloud.

With the preceding in mind, an example of an X-ray imaging system 10 suitable for acquiring data for reconstruction as discussed herein is provided in FIG. 1. As may be appreciated, the X-ray based imaging system 10 may be any suitable X-ray imaging modality, such as a computed tomography (CT) imaging system, a C-arm type imaging system, a tomosynthesis imaging system, a conventional radiography imaging system, a mammography imaging system, a fluoroscopy imaging system, and so forth.

In the embodiment illustrated in FIG. 1, imaging system 10 includes a source of X-ray radiation 12 and a detector 14. The X-ray source 12 may be an X-ray tube or comprise one or more other sources of X-ray radiation suitable for the acquisition of medical or other images. The X-rays 16 generated by the source 12 pass into an imaging region in which an object to be imaged (e.g., a part undergoing non-destructive evaluation or testing), a tissue sample to be imaged, a bag or package undergoing security screening, a patient undergoing an imaging protocol, and so forth may be positioned. In the illustrated example, a patient 18 undergoing imaging is positioned within the imaging volume during a procedure. In the depicted example, the X-rays 16 are collimated to be a fan-shaped (planar) or cone-shaped (volumetric) beam, e.g., a fan-beam or cone-beam, which passes through the imaged volume.

A portion of the X-ray radiation 20 passes through or around the patient 18 (or other subject of interest) and impacts a detector array, represented generally as the detector 14. Detector elements (e.g., pixels) of the detector 14 produce electrical signals that represent the intensity of the incident X-rays 20 upon detector elements of detector 14. These signals are acquired and processed, as discussed herein, to reconstruct images of the features within the patient 18.

With respect to the detector 14 as used herein, various types of detectors are contemplated that may be suitable for phase-contrast imaging in accordance with the present invention. In general, a detector 14 as used herein will comprise an array of pixels. Each pixel is associated with some medium with which X-rays interact and with sub-pixel resolution electrodes that measure some property or signal generated in response to the interaction of the X-rays with the medium. In certain embodiments as discussed herein, the electrodes associated with a given pixel are in an interleaved or other discontinuous configuration (i.e., not a 1-dimensional or two-dimensional array of contiguous electrodes) that in practice provides the ability to discriminate signal at sub-pixel resolutions within a given pixel, which may in certain implementations be leveraged to provide functionality comparable to what might be achieved by providing an analyzer grating at the surface of the detector 14.

In the context of a scintillator-based embodiment (e.g., in embodiments where a scintillator is used to convert high-energy X-ray photons to lower energy optical photons that are detected), the electrodes associated with each pixel may take the form of an interlaced or other discontinuous photodiode electrode structure suitable for reading out signals generated in response to the optical photons. In the context of a direct-conversion detector (i.e., a detector where the X-ray photons are themselves detected and generate a responsive signal, such as via interaction with a semiconductor material, as opposed to a secondary photon generated by a scintillator), the electrodes associated with each pixel may similarly be provided as an interlaced or other non-continuous set of electrodes. Such direct-conversion type detectors may be configured to provide certain additional functionality, such as being energy-integrating and/or photon-counting type detectors. In photon-counting contexts, the coincidence detection and/or spectral information may also be acquired using the detector 14.

In the depicted example gratings 22, 24 (e.g., absorption or phase gratings) are positioned in the path of the X-ray beam. The grating 22 or 24 may be the only grating provided if the source 12 is sufficiently small and/or is coherent. The grating 24 may be either in front of (grating 82 in FIG. 2) or behind (grating 24 in FIG. 1) the patient 18. In practice however, an additional source-side grating may be present near the source 12 to effectively cause a larger and/or incoherent source 12 to be perceived as a multitude of spatially-coherent line sources in a phase-contrast context. Such gratings may be present to facilitate phase-contrast imaging. In the depicted example, the grating 24 opposite the patient 18 relative to the source 12 (i.e., on the detector-side) is also provided.

In the present example, the source 12 and detector 14 (as well as any gratings, filters, collimators, and so forth) may be a part of an imager subsystem 30. In certain imaging modalities (e.g., computed tomography (CT), C-arm angiography, tomosynthesis), the source 12 and detector 14 of the imager 30 may be moved relative to the patient or imaged object along one or more axes during a scan procedure for which projection data is acquired. For example, the imager 30 may move about a first axis of rotation, a second axis of rotation, or a third axis of rotation, or any combination thereof. In one embodiment, the translation and rotation of the imager 30 may be determined or coordinated in accordance with a specified protocol. Alternatively, the imager 30 may be held constant, while the object is repositioned, such as in non-destructive testing applications.

The movement of the imager 30, if any, may be initiated and/or controlled by one or more linear/rotational subsystems 46. The linear/rotational subsystems 46 may include support structures, motors, gears, bearings, and the like, that enable the relative rotational and/or translational movement of the imager 30. In one embodiment, the linear/rotational subsystems 46 may include a structural apparatus (e.g., a C-arm, rotating gantry, turntable, and so forth) supporting the source 12 and the detector 14 or, alternatively, the object or patient 18.

A system controller 48 may govern the linear/rotational subsystems 46 that initiate and/or control the movement of the components of the imager 30. In practice, the system controller 48 may incorporate one or more processing devices that include or communicate with tangible, non-transitory, machine readable media collectively storing instructions executable by the one or more processors to facilitate performance of imaging operations. The system controller 48 may also include features that control the timing of the activation of the source 12, for example, to control the acquisition of X-ray data obtained during a particular imaging sequence. The system controller 48 may also execute various signal processing and filtration functions, such as for initial adjustment of dynamic ranges, interleaving of digital projection data, and so forth. Therefore, in general, the system controller 48 may be considered to command operation of the imaging system 10 to execute examination protocols. It should be noted that, to facilitate discussion, reference is made below to the system controller 48 as being the unit that controls acquisitions, movements, and so forth, using the imager 30. However, embodiments where the system controller 48 acts in conjunction with other control devices (e.g., other control circuitry local to the imagers or remote to the system 10) are also encompassed by the present disclosure.

In the present context, the system controller 48 includes signal processing circuitry and various other circuitry that enables the system controller 48 to control the operation of the imager 30 and the linear/rotational subsystems 46. In the illustrated embodiment, the circuitry may include an X-ray controller 50 configured to operate the X-ray source 12. Circuitry of the system controller 48 may also include one or more motor controllers 52. The motor controllers 52 may control the activation of various components that are responsible for moving the source 12 and the detector 14. In other words, the motor controllers may implement a particular acquisition trajectory or motion for the relative motion of the components of the imager 30.

The system controller 48 is also illustrated as including one or more data acquisition systems 54. Generally, the detector 14 may be coupled to the system controller 48, and more particularly to the data acquisition systems 54. The data acquisition systems 54 may receive data collected by readout electronics of the detector 14 and in certain embodiments may process the data (e.g., by converting analog to digital signals or to perform other filtering, transformations, or similar operations).

It should be noted that the tangible, non-transitory, machine-readable media and the processors that are configured to perform the instructions stored on this media that are present in the system 10 may be shared between the various components of the system controller 48 or other components of the system 10. For instance, as illustrated, the X-ray controller 50, the motor controller 52, and the data acquisition systems 54 may share one or more processing components 56 that are each specifically configured to cooperate with one or more memory devices 58 storing instructions that, when executed by the processing components 56, perform image acquisition and reconstruction techniques. Further, the processing components 56 and the memory components 58 may coordinate in order to perform various image reconstruction processes.

The system controller 48 and the various circuitry that it includes, as well as the processing and memory components 56, 58, may be accessed or otherwise controlled by an operator via an operator workstation 60. The operator workstation 60 may include any application-specific or general-purpose computer that may include one or more programs (for example one or more imaging programs) capable of enabling operator input for the techniques described herein. The operator workstation 60 may include various input devices such as a mouse, a keyboard, a trackball, or any other similar feature that enables the operator to interact with the computer. The operator workstation 60 may enable the operator to control various imaging parameters, for example, by adjusting certain instructions stored on the memory devices 58.

The operator workstation 60 may be communicatively coupled to a printer 62 for printing images, patient data, and the like. The operator workstation 60 may also be in communication with a display 64 that enables the operator to view various parameters in real time, to view images produced by the acquired data, and the like. The operator workstation 60 may also, in certain embodiments, be communicatively coupled to a picture archiving and communication system (PACS) 66. Such a system may enable the storage of patient data, patient images, image acquisition parameters, and the like. This stored information may be shared throughout the imaging facility and may also be shared with other facilities, for example, a remote client 68. The remote client 68 may include hospitals, doctors' offices, or any other similar client.

Figure 2:
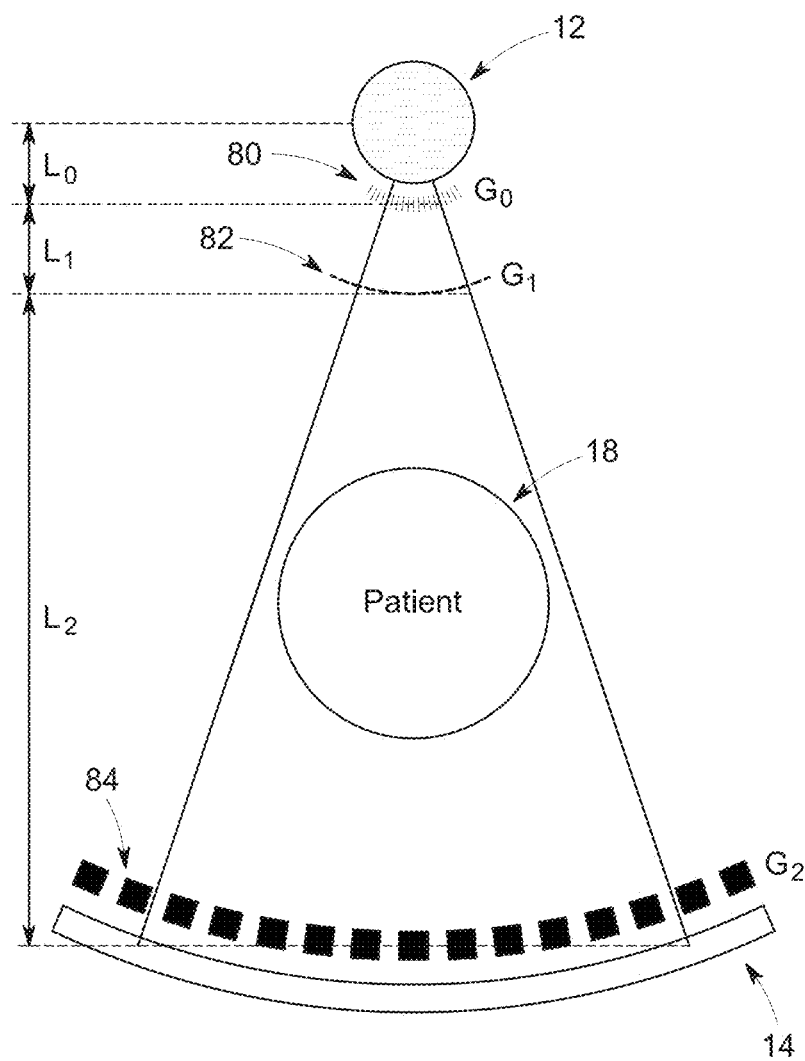
FIG. 2 depicts an example of a phase-contrast imaging system employing three gratings.

Various aspects of the present approaches may be further appreciated with respect to FIG. 2, which depicts features of a conventional phase-contrast imaging technique. Such phase-contrast imaging techniques typically determine a phase-shift angle for each voxel by comparing a spatial interference pattern observed with an object in the beam path with the spatial interference pattern when the object is absent. In the context of a conventional phase-contrast computed tomography (CT) imaging system, aspects of which are shown in FIG. 2, gratings (typically three gratings) may be employed to generate the interference patterns. In this example, a source-side grating G0 (denoted by reference number 80) is positioned near X-ray source 12 to ensure spatial coherence and effectively creates an array of individually coherent, but mutually incoherent emissions in response to operation of an incoherent X-ray source. A phase object in the beam path causes a slight refraction for each coherent subset of X-rays. The angular deviation so introduced results in changes of the locally transmitted intensity through the pair of gratings G1 and G2 (denoted by reference numbers 82 and 84 respectively), which can be detected by an X-ray detector 14 (as shown in FIG. 1). In particular, grating G1 82 in such an arrangement is located between the source 12 and detector 14 and imprints a periodic interference pattern onto the wave front. The grating G2 84 is located proximate to the detector (i.e., G2 is a detector-side grating) and resolves sub-pixel resolution interference pattern modulations. In practice, the gratings may be manufactured from silicon wafers using photolithography and electroplating where appropriate.

Figure 3:
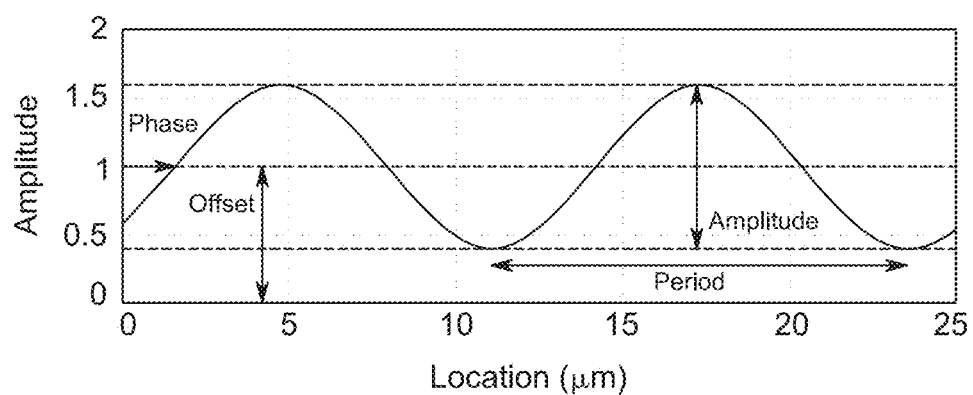
FIG. 3 depicts a generalized waveform illustrating parameters of a spatial interference pattern, in accordance with aspects of the present disclosure.

With respect to the spatial interference patterns created in phase-contrast imaging, and turning to FIG. 3, a brief explanation may be helpful in understanding the following discussion. In particular, the interference pattern created in phase-contrast imaging has three parameters that may be measured (period being known by design): (1) offset; (2) phase; and (3) amplitude. Offset as used herein results from the overall attenuation, as in conventional X-ray imaging. Phase is the spatial shift of the interference pattern relative to a reference, which corresponds to a gradient of the real part of the aggregate refractive index seen by an X-ray passing through an object under test. Amplitude of the interference pattern is the difference between the peaks and the valleys of the pattern, which may be reduced in the presence of microstructure. These three parameters are illustrated in FIG. 3 in the context of a sample pattern or waveform.

With the preceding in mind, while the arrangement shown in FIG. 2 is suitable for phase-contrast imaging, such an arrangement may necessitate high X-ray flux since some portion of the X-rays are absorbed by each of the three gratings, reducing the flux that reaches the detector 14. By way of example, in contrast to conventional CT (i.e., absorption based imaging) where all of the X-ray flux reaches the detector 14 (absent that portion absorbed by the patient 18), in grating-based phase-contrast imaging only a limited portion (e.g., 25%) of the emitted flux may reach the detector 14 due to incidental absorption by the various gratings. In a medical context, this may result in higher flux being employed in order to freeze patient motion and obtain useful images. Grating G2 84 absorbs part of the X-ray flux that passes through the patient, thereby reducing dose efficiency of the imager subsystem 30.

Figure 4:
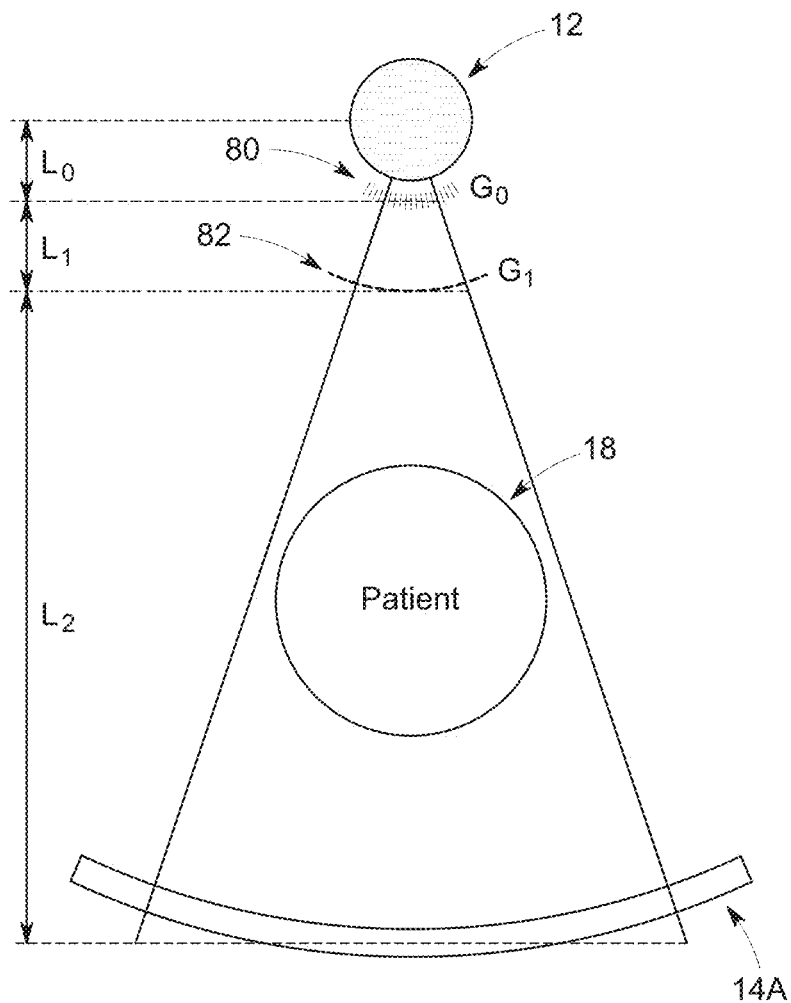
FIG. 4 depicts an example of a phase-contrast imaging system employing two gratings and a phase-sensitive detector, in accordance with aspects of the present disclosure.

To reduce the loss of flux attributable to the gratings in phase-contrast imaging, the present invention eliminates the detector-side grating G2 84 and integrates the functionality of this grating into a phase-sensitive detector 14A, as shown in FIG. 4. In addition to eliminating the loss of X-ray flux (and associated patient dose) due to X-ray absorption by grating G2, this technique has the further benefit of eliminating the need to take multiple acquisitions at different phase steps, as is typical in a phase-contrast imaging protocol. In particular, in a conventional phase-contrast imaging acquisition, when an analyzer grating G2 84 is used in front of a standard CT detector, only a single measurement can be taken for each pixel at each time. For this reason, the analyzer grating G2 84, with apertures at a periodicity equaling the frequency of the interference pattern, is typically shifted, and additional (e.g., 3 total measurements) subsequent measurements are taken. By employing a phase-sensitive detector 14A (e.g., a detector in which multiple pixel electrodes provide sub-pixel resolutions corresponding to the period of the interference pattern, as discussed in greater detail below), all 3 independent measurements can be taken simultaneously.

Figure 5:
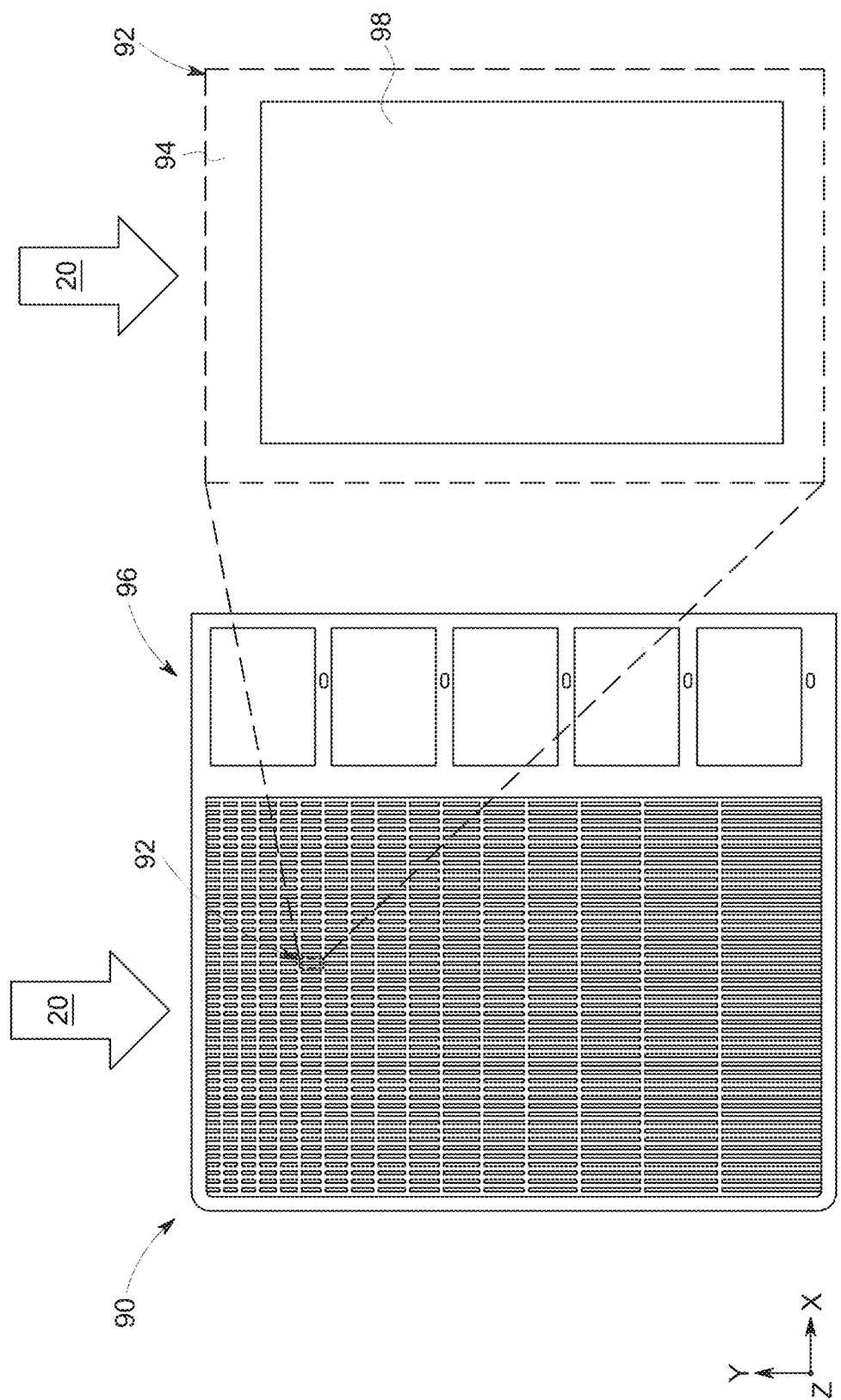
FIG. 5 depicts an example of a detector module and pixel.
Figure 6:
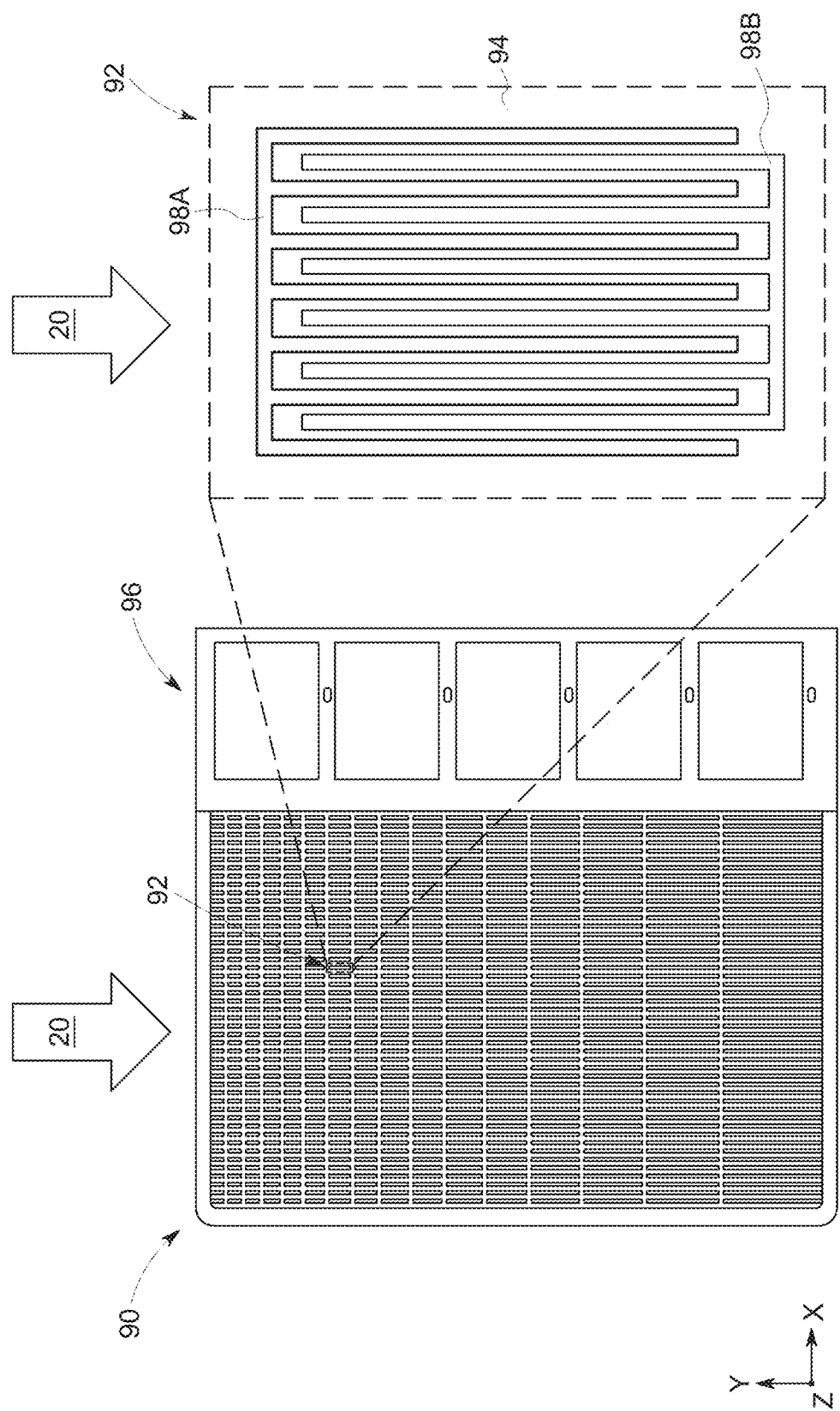
FIG. 6 depicts an example of a phase-sensitive detector module, in accordance with aspects of the present disclosure.
Figure 7:
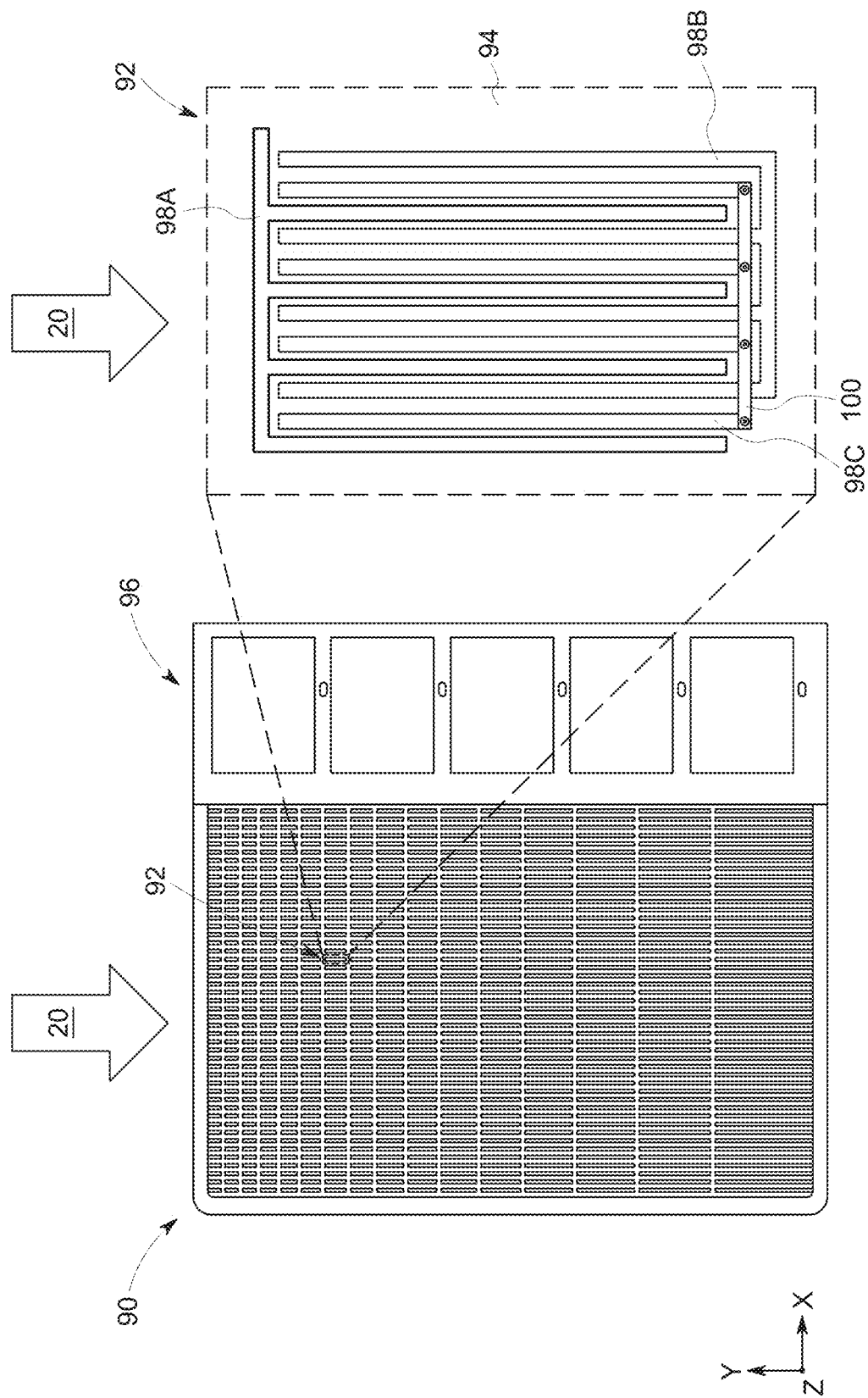
FIG. 7 depicts another example of a phase-sensitive detector module, in accordance with aspects of the present disclosure.

With this in mind, FIGS. 5, 6, and 7 depict examples of a detector module 90 that may be used to form a detector 14A and of pixels 92 provided in the detector module 90. In one embodiment, the detector module 90 comprises a plurality of pixels 92 formed using silicon, cadmium zinc telluride (CZT), cadmium telluride (CdTe), or other suitable detector materials that generate signal in response to X-rays without a scintillator intermediary component, i.e., direct-conversion detector materials. As shown in FIGS. 5-7, the pixels 92 may increase in length in the direction of the X-ray beam path 20 so as to allow similar response at different depths within the detector. Alternatively, a single, long pixel may be provided that aligns with the direction of the X-ray beam. Readout circuitry 96 is depicted as being provided on the side or bottom of the detector module 90 so that detector modules 90 can be combined side-to-side or end-to-end to provide a large or configurable field-of-view.

With respect to these figures, FIG. 5 depicts a detection or conversion material 94 (such as a semiconductor material) associated with the pixel 92 with which X-rays interact. In the example of FIG. 5, within a respective pixel a single, continuous electrode 98 is associated with the conversion material 94 of the pixel 92. Conversely, FIGS. 6 and 7 depict that within a respective pixel 92, multiple, non-continuous electrodes 98A, 98B, and 98C are associated with the conversion material 94 of each respective pixel 92 to provide sub-pixel resolution measurements. In the depicted example, the electrodes of FIGS. 6 and 7 are provided as interlaced comb patterns, which may in one embodiment have sub-pixel resolution distances and separations corresponding to the frequency of the spatial interference pattern for a given phase-contrast imaging system. In certain embodiments, the electrodes have sub-pixel resolution distances and separations that are larger than a frequency of the spatial interference pattern for a given phase-contrast imaging system but small enough to enable charge sharing between adjacent sub-pixel resolution readout structures (e.g., electrodes) when an X-ray photon hits between adjacent sub-pixel resolution readout structures (see FIG. 8). For example, the sub-pixel resolution distances and separations may be larger than the frequency of the spatial interference pattern by an integer multiple (e.g., 2, 3, etc.).

For example, in FIG. 6 the electrodes 98A and 98B form a pattern of alternating arms comprising two interleaved combs. In FIG. 7 the electrodes 98A, 98B, and 98C form a pattern of alternating arms comprising three interleaved combs, one of which is spanned by a conductive bridge 100 provided outside the plane of the other conductive traces so as to allow separate electrical connection to each electrode. It may be noted that embodiments in which all pixels 92 of the detector module 90 have multiple, sub-pixel resolution electrodes are contemplated as well as embodiments in which only some of the pixels 92 of the detector module 90 have multiple, sub-pixel resolution electrodes, such as some or all of the pixels 92 in the center of the detector module 90. As discussed herein, the interlaced patterns of the electrodes 98 may have a spacing corresponding to the period of the phase-contrast interference pattern, thus allowing all three parameters of interest (i.e., offset, phase, and amplitude) to be measured simultaneously, as opposed to requiring multiple, discrete measurements in which an analyzer grating is shifted, requiring added acquisition time and patient dose.

Although a pattern of two and three interleaved sub-pixel resolution electrodes are shown in FIGS. 6 and 7, respectively, alternate configurations using additional interleaved sub-pixel resolution electrodes as needed to accurately estimate the phase-contrast signals are contemplated.

The direction in which the electrodes 98 (or other patterned features, such as photodiodes) run may vary depending on the embodiment and may be either in the direction of the X-ray beam 20 (as shown) or orthogonal to the X-ray beam 20. When running parallel to the X-ray beam 20, the lines of the combs 98 form a line pattern in the direction of the X-ray beam 20, as shown in FIGS. 6 and 7. Conversely, when the pattern features are orthogonal to the X-ray beam 20, any pattern may be employed, including a coded aperture, that has spacing corresponding to the phase-contrast interference pattern, as noted above.

Figure 8:
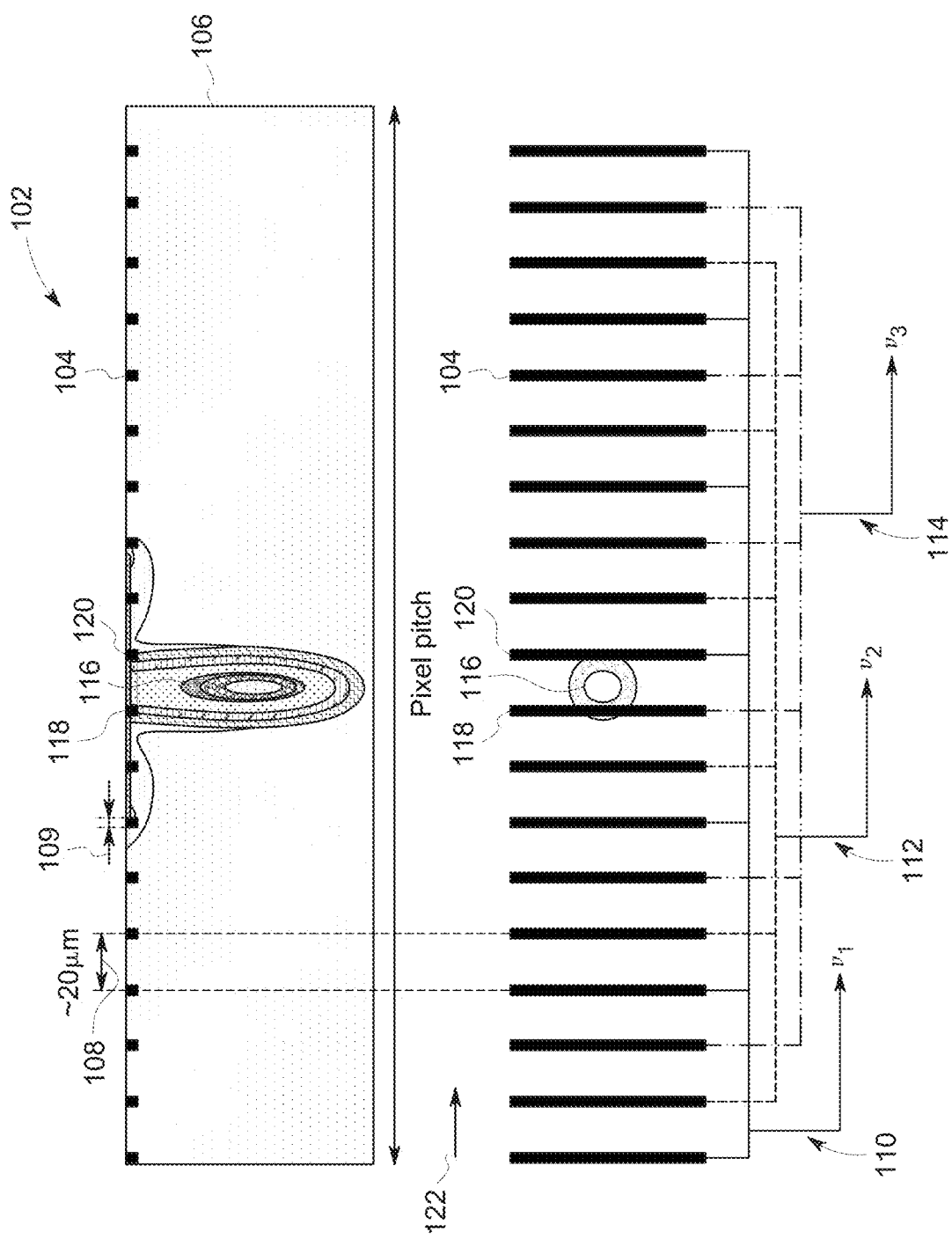
FIG. 8 depicts side and top view of a phase-sensitive detector module experiencing an electron charge cloud from an incident X-ray photon, in accordance with aspects of the present disclosure.

FIG. 8 depicts side and top views of a phase-sensitive detector module experiencing an electron charge cloud from an incident X-ray photon. The side view is located above and the top view is located below. In certain embodiments, (e.g., in an edge-illuminated detector), the above portion may be the top view and the bottom portion may be the side view. A single detector pixel 102 (consisting of N sub-pixels) of a photon-counting detector is illustrated with the side view illustrating electrodes 104 (e.g., sub-pixel resolution electrodes) in a comb arrangement, as described above, disposed on a detector material 106 (e.g., CZT, CdTe, or other suitable direct-conversion detector material) that generates signal in response to X-rays without a scintillator intermediary component. It should be noted that the electrode sampling pitch can be electronically set during readout to match the requirements for performing phase-contrast imaging. The sub-pixel electrode 104 are separated or spaced apart at a distance 108 that is larger than a frequency of the spatial interference pattern for the phase-contrast imaging system but small enough to enable charge sharing between adjacent sub-pixel resolution electrodes 104 when an X-ray photon hits between adjacent sub-pixel resolution electrodes 104. For example, the sub-pixel resolution distances and separations may be larger than the frequency of the spatial interference pattern by an integer multiple (e.g., 2, 3, etc.). As depicted, the distance 108 is approximately 5 to 50 μm. Each sub-pixel resolution electrode 104 has a width 109 that is less than the distance 108.

The bottom view only illustrates the arrangement of the sub-pixel resolution electrodes 104 with associated readout pathways 110, 112, and 114 corresponding to different phases (e.g., phase 1, phase 2, and phase 3) of the spatial interference pattern. In other words, the combs are grouped into three and coupled to output wires connected to respective application-specific integrated circuit (ASIC) channels. The readout pathways are 110, 112, and 114, and they are associated with the signals or voltages, $v_1$, $v_2$, and $v_3$, respectively.

As depicted, a single X-ray event due to an incident X-ray photon as indicated by electron charge cloud 116 has hit the detector between adjacent sub-pixel resolution electrodes 118, 120. Thus, the charge is shared between the electrodes 118, 120. For a single X-ray event (such as event 116), the three ASIC channels (phases) register different charges, depending on the location of the charge cloud 16. As more and more events are registered, the three phase signals are accumulated, resulting in the desired output. Signals for corresponding (i.e., same phase) sub-pixel electrodes 104 are combined to form the "phase" comb in either the pre-readout (i.e., the analog) domain or the post-readout (i.e., digital) domain. The location or point of interaction of the detection event in a lateral direction 122 (e.g., X-direction) may be estimated based on the electrical crosstalk signals (e.g., $v_1$, $v_2$, and $v_3$). The phase may also be estimated from the point of interaction. With adequate charge sharing in the photon-counting detector, it is possible to determine the exact location of each detector event (even when utilizing larger pixels and, thus, larger sub-pixel electrodes). The larger period of the electrode pattern may make manufacturing easier.

In alternate embodiments (e.g., FIG. 9), the sub-pixel resolution electrodes 104 may be associated with two separate readout pathways 110 and 112 corresponding to different phases (e.g., phase 1 and phase 2) of the spatial interference pattern. In other words, the combs are grouped into two and coupled to output wires connected to respective application-specific integrated circuit (ASIC) channels. The readout pathways 110 and 112 are associated with the signals or voltages, $v_1$ and $v_2$, respectively.

Figure 10A:
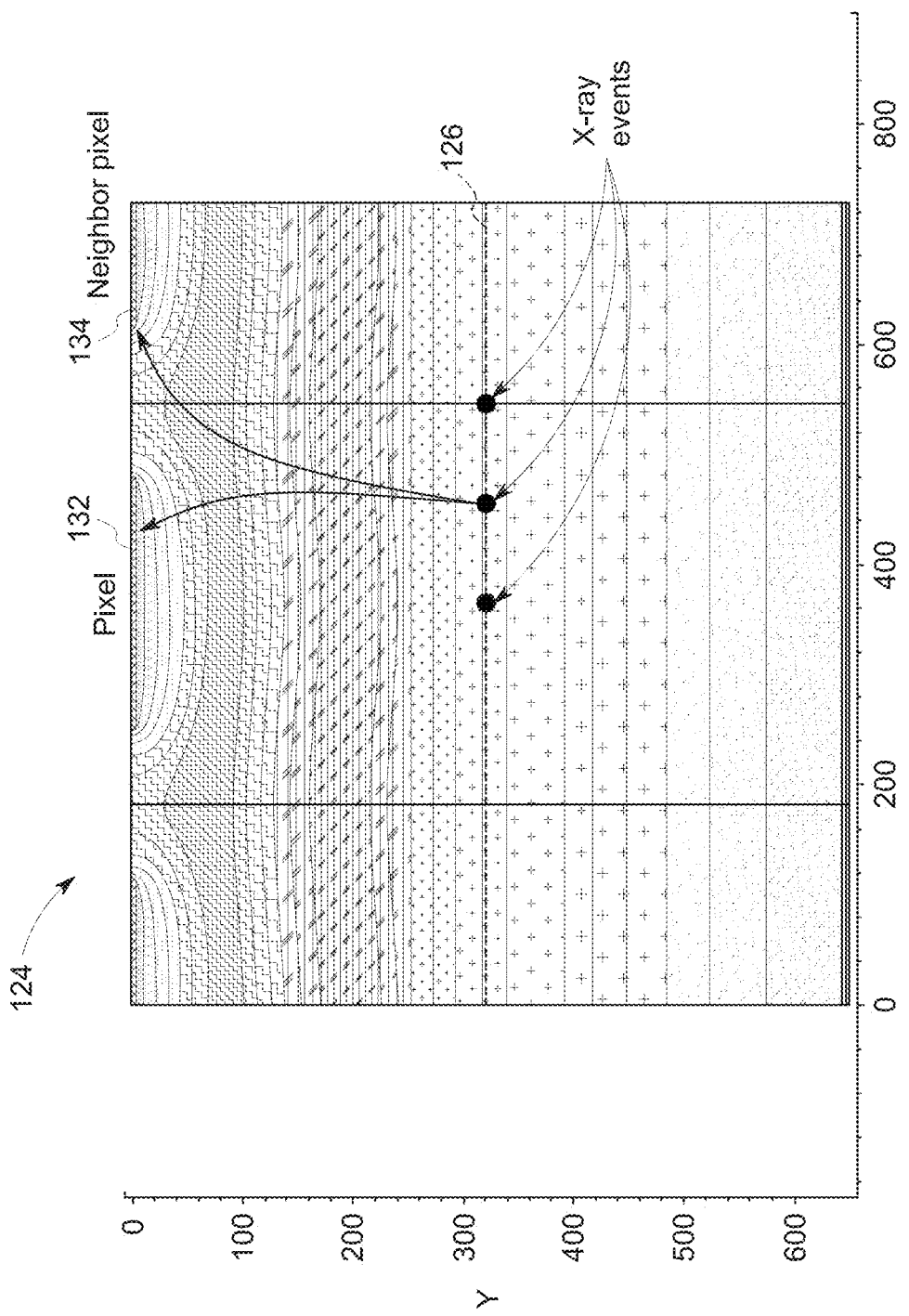
FIGS. 10A-10C depict how an X-ray point of interaction is estimated based on comb signals, in accordance with aspects of the present disclosure.
Figure 10B:
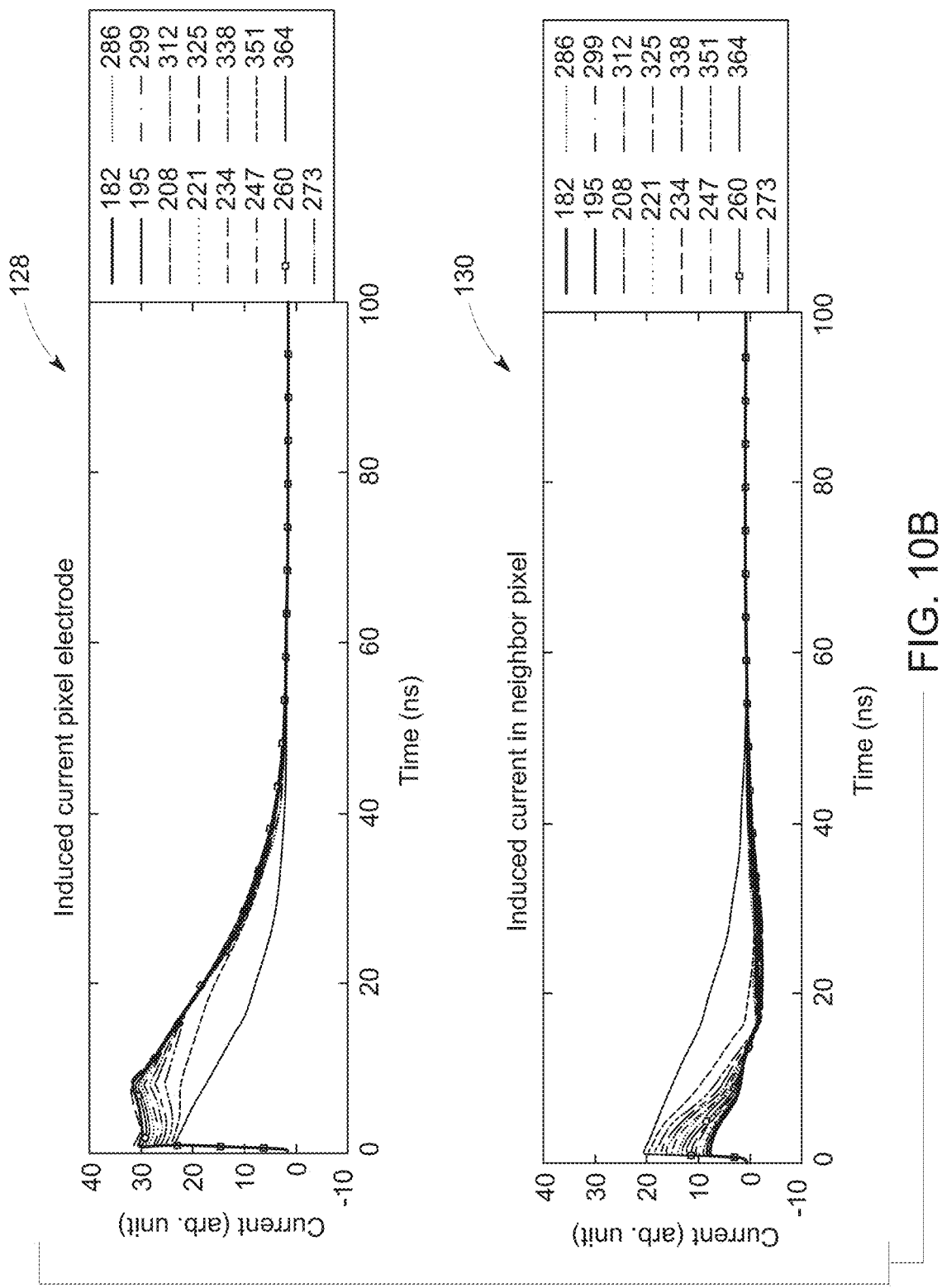
Figure 10C:
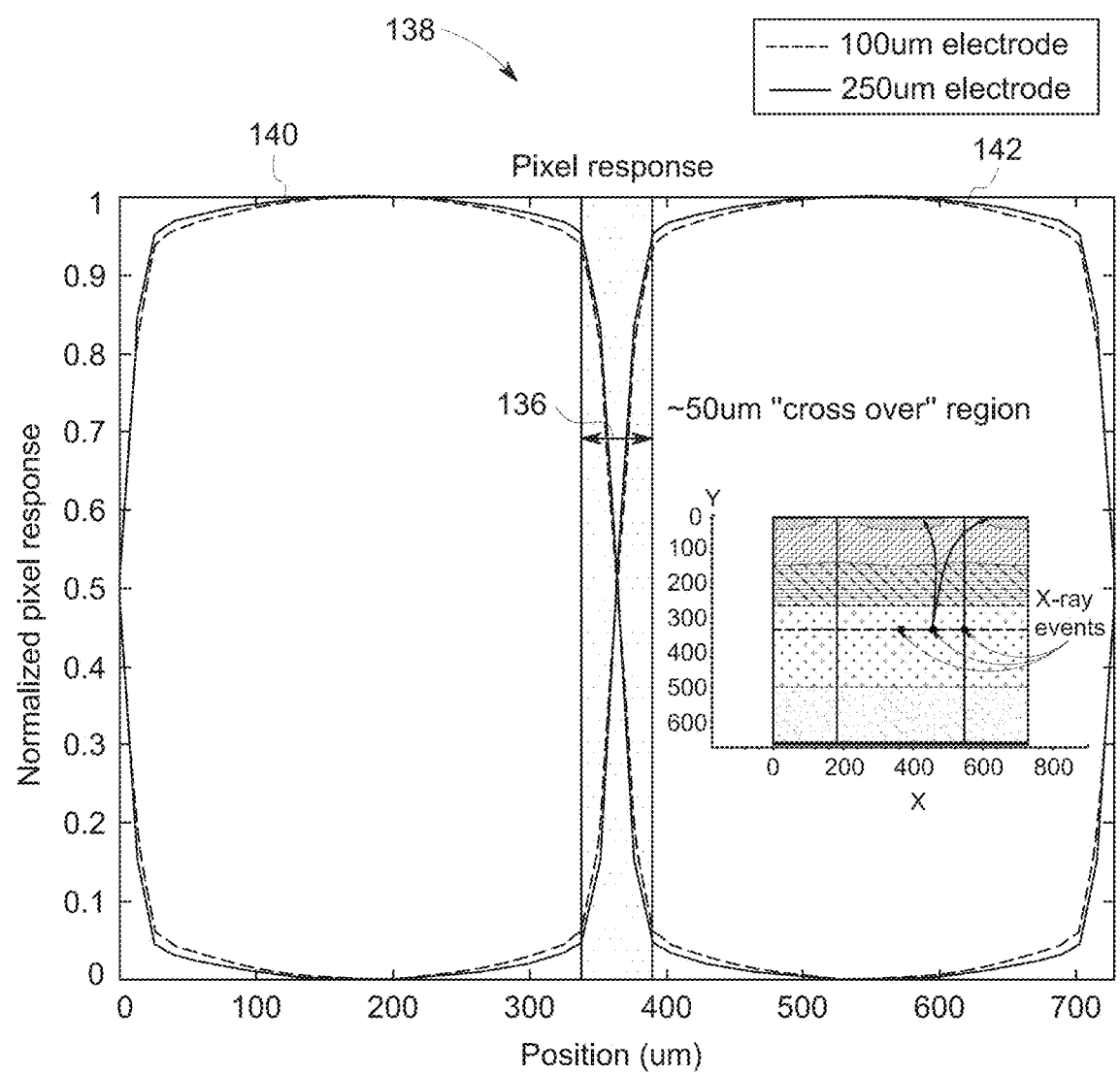

FIGS. 10A-10C depict how an X-ray point of interaction is estimated based on comb signals. The image 124 in FIG. 10A indicates the different spatial locations of an X-ray event at the time of 1 nanosecond in a pixel center plane 126. Graphs 128 and 130 in FIG. 10B illustrate the induced currents for the sub-pixel electrodes associated with a pixel electrode (e.g., pixel 128 in image 124) and a neighboring pixel electrode (e.g., pixel 130 in image 124), respectively. The X-ray point of interaction (e.g., in the lateral direction (e.g., x in image 124)) may be estimated from the electrical crosstalk signal in region 136 in image 138 in FIG. 10C. Image 134 illustrates the normalized pixel response (e.g., for different sized electrodes) between the pixel 132 (represented by plot 140) and the neighboring pixel 134 (represented by plot 142).

Figure 11:
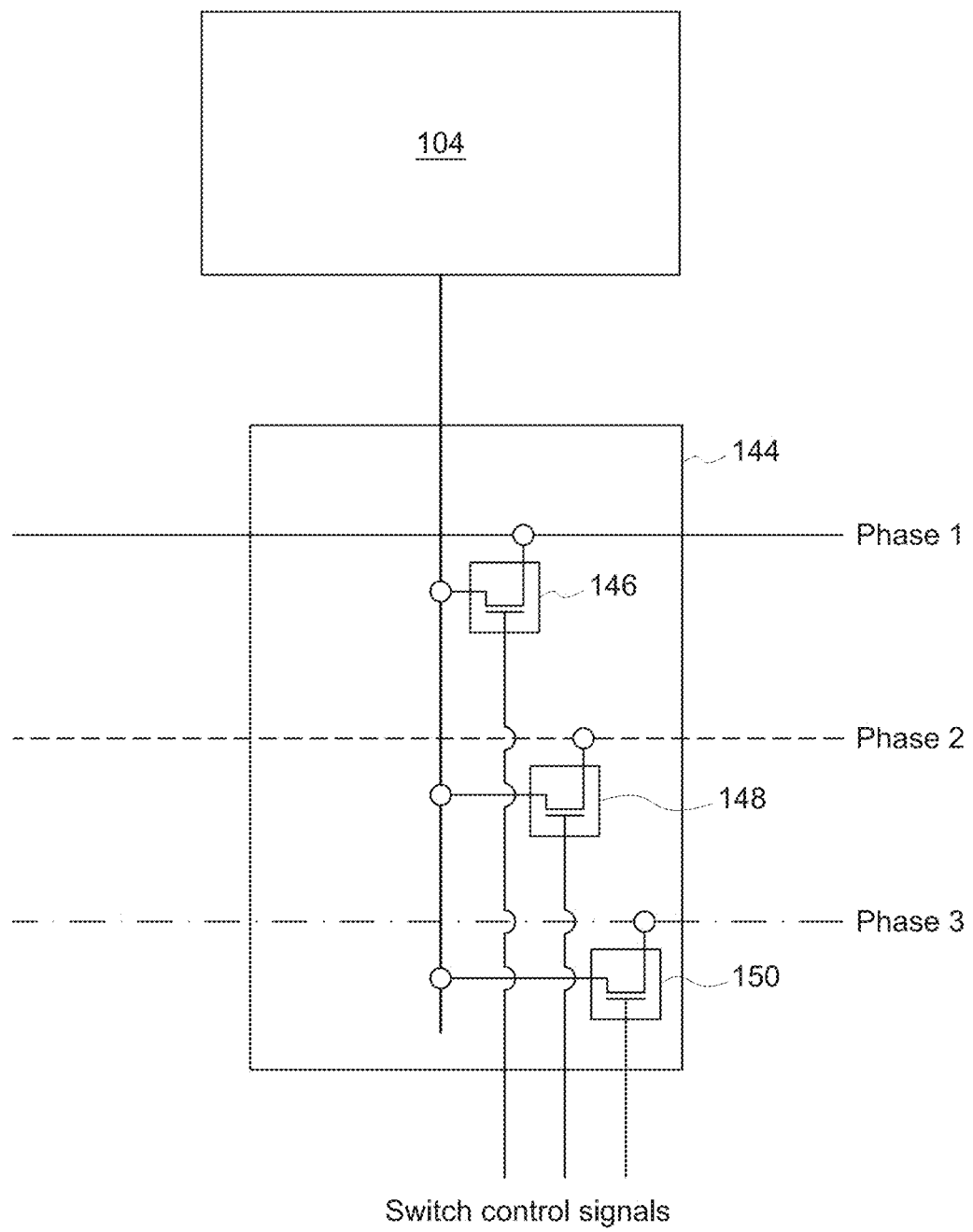
FIG. 11 depicts a sub-pixel electrode coupled to a 3-way switch, in accordance with aspects of the present disclosure.

In certain embodiments, each sub-pixel electrode 104 (e.g., of the detectors depicted in FIGS. 8 and 9) is coupled to a 3-way switch matrix as depicted in FIG. 11. FIG. 11 depicts a 3-way switch 144 coupled to the sub-pixel electrode 104. The 3-way switch 144 includes transistors 146, 148, and 150. Each transistor 146, 148, and 150 is associated with phase 1, phase 2, and phase 3, respectively. When a particular transistor is opened, the signal is connected to the respective phase associated with that transistor. For example, if transistor 146 was opened, the signal from the sub-pixel electrode 104 would be connected to phase 1. Switch control signals (e.g. from a controller) are provided from a controller (e.g., of a detector) to the transistors 146, 148, 150 to open/close the transistors with respect to the sub-pixel electrodes 104. The 3-way switch 144 enables the sub-pixel electrode 104 (and other sub-pixel electrodes 104) to be selectively connected to any of the three phases. Thus, the comb arrangement of the sub-pixel electrodes 104 may be selectively configured so that certain sub-pixel electrodes may be selectively connected to a different phase of the spatial interference pattern. This allows configuration of sub-pixel electrode "strips" into comb arrangements of different periods. This may be advantageous in situations where the period of the phase contrast interference pattern changes, such as between two different tube voltage settings, or when phase contrast sensitivity of the X-ray system is adjusted by changing the period and/or position of the other system components (generally gratings G0 and G1).

Figure 9:
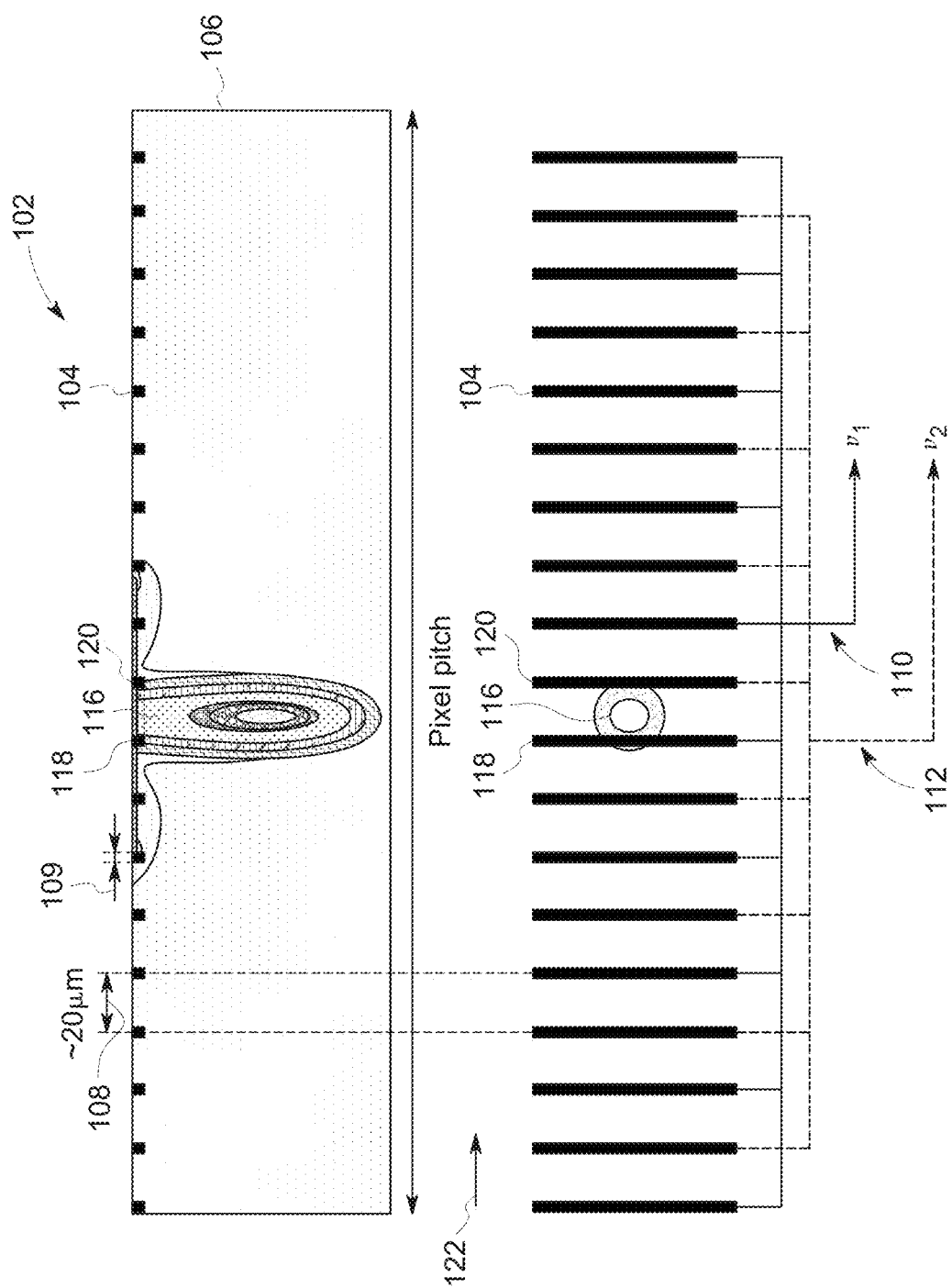
FIG. 9 depicts side and top view of a phase-sensitive detector module experiencing an electron charge cloud from an incident X-ray photon (e.g., having two readout pathways), in accordance with aspects of the present disclosure.
Figure 12:
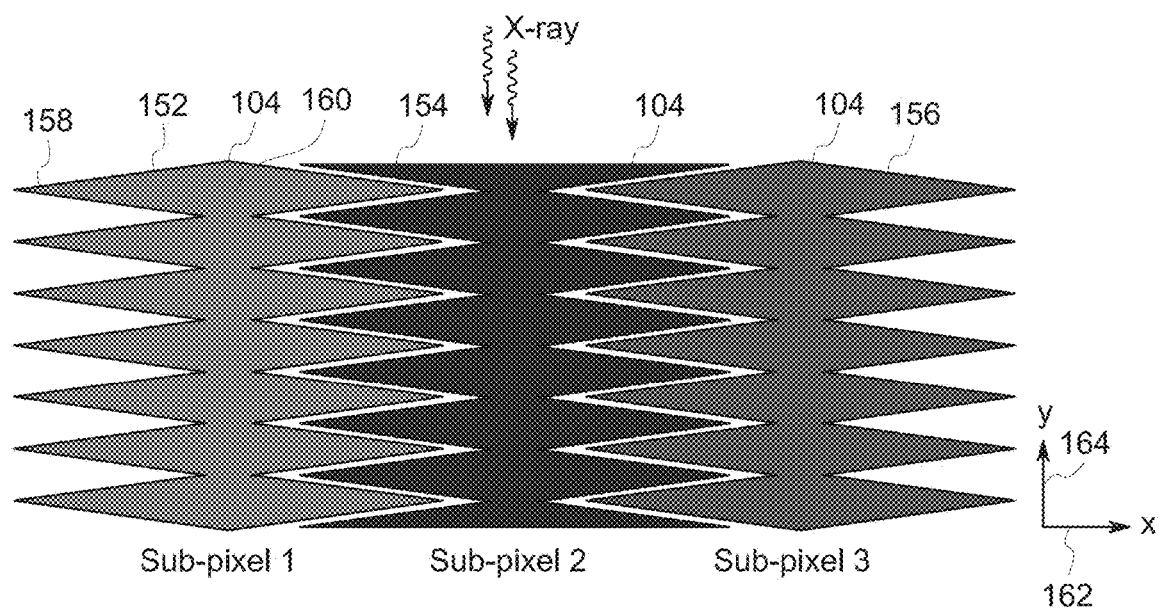
FIG. 12 depicts adjacent sub-pixel electrodes having an interlocked triangular pattern between them (e.g., continuous sub-pixel electrodes), in accordance with aspects of the present disclosure.
Figure 14:
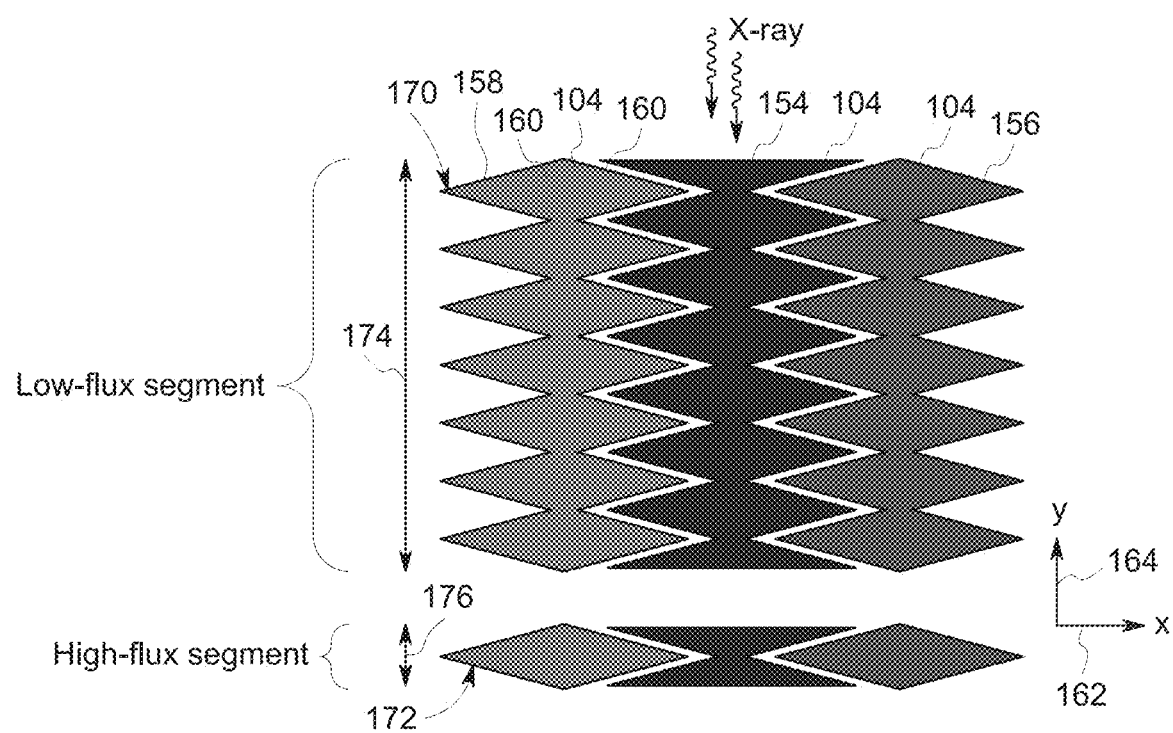
FIG. 14 depicts adjacent sub-pixel electrodes having an interlocked triangular pattern between them (e.g., segmented sub-pixel electrodes), in accordance with aspects of the present disclosure.

In certain embodiments, the photon-counting detectors such as an edge-illuminated detector or phase-contrast detectors (e.g., as depicted in FIGS. 8 and 9) may improve their resolution and increase their charge sharing to better determine the exact location of each detection event. FIGS. 12 and 14 depict configurations of sub-pixel electrodes that may improve resolution and increase charge sharing. Indeed, the configurations in FIGS. 12 and 14 may depict configurations for the sub-pixel electrodes that enable controlled charge sharing with a linear transfer function between the location of the event and the amount of charge in each sub-pixel electrode 104. In certain embodiments, the depicted configurations in FIGS. 12 and 14 may apply to pixel electrodes.

FIG. 12 depicts adjacent sub-pixel electrodes 104 having an interlocked triangular pattern between them. Three sub-pixel electrodes 104 (e.g., sub-pixel electrode 152 (sub-pixel 1), sub-pixel electrode 154 (sub-pixel 2), and sub-pixel electrode 156 (sub-pixel 3) are depicted in FIG. 12. Each sub-pixel electrode 104 is a continuous electrode. Each sub-pixel electrode 104 includes a plurality of tapered portions 158 (e.g., triangular portions) extending from both sides of a central portion 160 in a direction 162 (e.g., x-direction). As depicted in FIG. 12, the direction 162 is orthogonal to a path of X-ray photons (e.g., as in an edge-illuminate detector). In certain embodiments, depending on the type of detector, the path of the X-rays may be into the paper relative to the sub-pixel electrodes 104 (i.e., orthogonal to the plane of the horizontal plane of the sub-pixel electrodes 104).

The tapered portions 158 of one sub-pixel electrode 104 fit in between the tapered portion 158 of an adjacent sub-pixel electrode 104 in an interlocked triangular pattern. For example, the tapered portions 158 of the sub-pixel electrode 152 fit between the tapered portions 158 of the sub-pixel electrode 154 and vice versa. Also, the tapered portions 158 of the sub-pixel electrode 154 fit between the tapered portions 158 of the sub-pixel electrode 156 and vice versa. Due to the interlocked triangular pattern, adjacent sub-pixel electrodes overlap both in the direction 162 and in a direction 164 (which is orthogonal to direction 162).

Figure 13A:
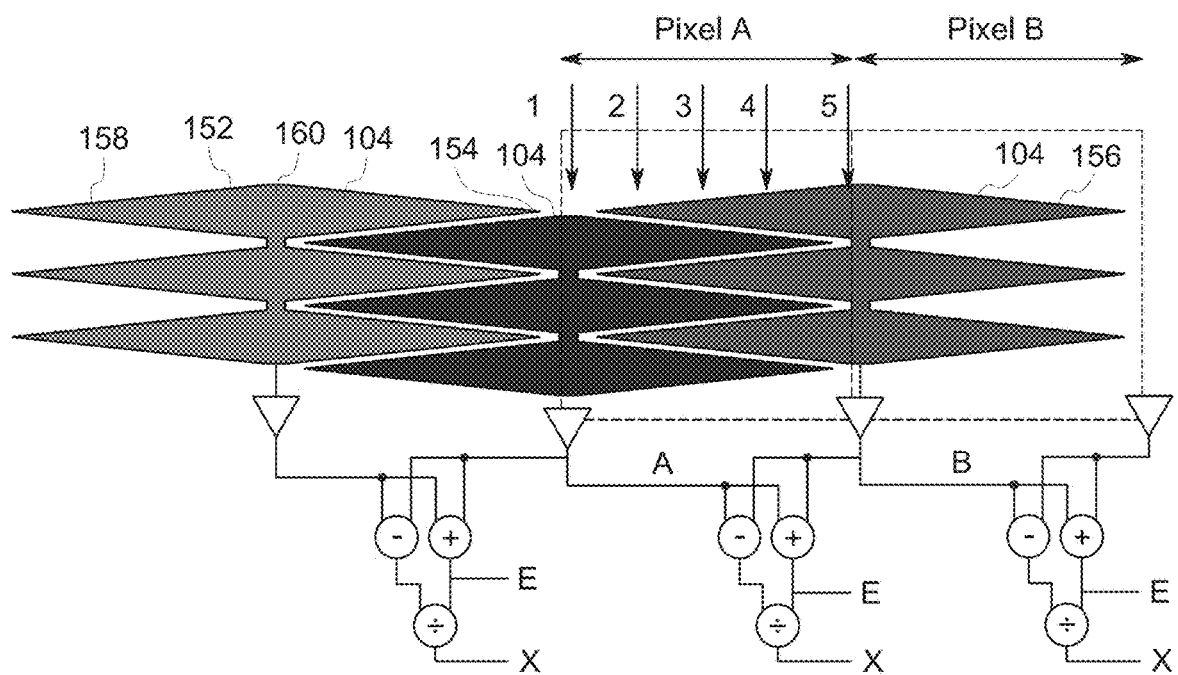
FIGS. 13A and 13B depict how charge sharing is defined between the adjacent sub-pixel electrodes having an interlocked triangular pattern between them; in accordance with aspects of the present disclosure.
Figure 13B:
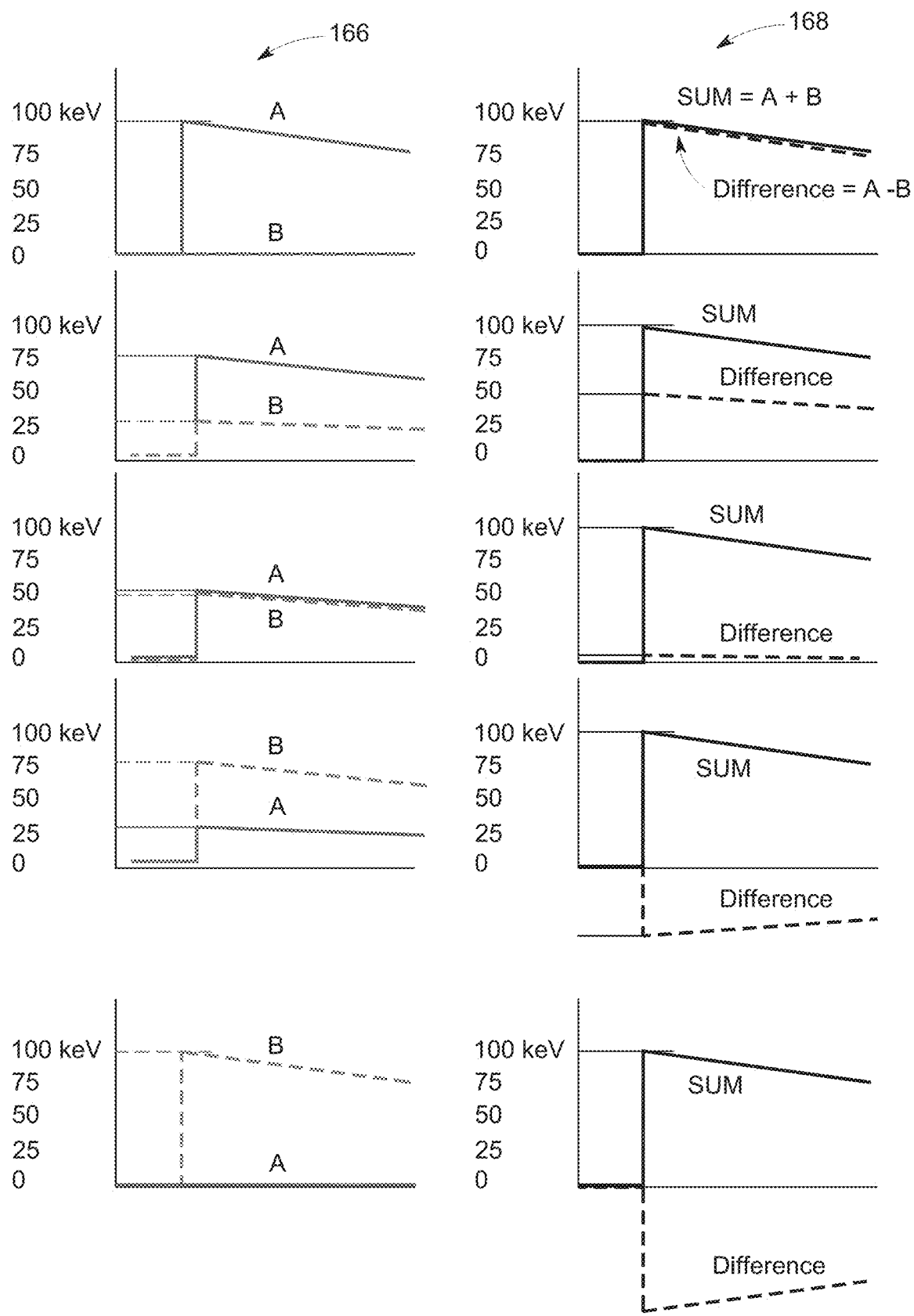

The interlocked triangular pattern enables charge sharing (e.g., controlled charge sharing) between the adjacent sub-pixel electrodes 104 to determine a location of each detection event in the direction 162 based on the charges received in each sub-pixel electrode 104. In particular, the interlocked triangular pattern defines the charge sharing between the adjacent sub-pixel electrodes 104 so that a charge in each adjacent pixel is a linear function of location between centers (e.g., center portions 160) of the sub-pixel electrodes 104. FIGS. 13A and 13B depict how charge sharing is defined between the adjacent sub-pixel electrodes 104 having an interlocked triangular pattern between them. Sub-pixel electrodes 154 and 156 are designated Pixel A and Pixel B, respectively, in FIG. 13. FIG. 13A depicts the readout circuitry coupled to Pixel A and Pixel B and relative locations of incident X-ray photons on Pixels A and B designated 1, 2, 3, 4, and 5. FIG. 13B depicts a first column 166 of graphs of the respective X-ray energies measured at Pixels A and B for incident X-ray photons at locations 1, 2, 3, 4, and 5. FIG. 13B also depicts a second column 168 of graphs respective sum and difference between the X-ray energies measured at Pixels A and B for the incident X-ray photons at locations 1, 2, 3, 4, and 5. The total X-ray energy in Pixel A equals the sum of the X-ray energy in pixels A and B. A distance from a center of Pixel A (defined units of pixel pitch) equals $(A-B)/(A+B)$, where the illustrated range is 1 equals left edge, 0 equals center, and −1 equals right edge. As depicted in the graphs of columns 166 and 168 at location 1, the total X-ray energy completely occurs in Pixel A. At location 5, the total X-ray energy completely occurs in Pixel B. At location 3, the total X-ray energy is evenly split between Pixels A and B. At location 2, a greater portion of the total X-ray energy is attributed to Pixel A. At location 4, a greater portion of the total X-ray energy is attributed to Pixel B. These graphs in the columns 166 and 168 illustrate the linear function defining charge sharing between the centers (e.g., Locations 1 and 5) of Pixels A and B.

With charge sharing as illustrated in FIGS. 12, 13A, and 13B, each X-ray photon may create a detection event in two neighboring sub-pixel electrodes 104 (which may lower the maximum count rate of the detector). It should be noted, in order to get adequate charge sharing, the size of the charge cloud needs to be equal to or larger than a height of the triangular interlocking pattern (e.g., in direction 164). In the case of an edge-illuminated detector, depth segmentation may mitigate the count rate issue. FIG. 14 illustrates an alternative embodiment for the adjacent sub-pixel electrodes 104 in an interlocked triangular pattern. The sub-pixel electrodes 104 are segmented. As depicted, each sub-pixel electrode 104 includes a first segment 170 and a second segment in a co-linear arrangement along the direction 164. The first segment 170 is located above the second segment 172 so that it encounters X-ray photons first. As depicted, the first segment 170 is longer in the direction 164 than the second segment 172 (i.e., length 174 is greater than length 176). Thus, the first segment 170 receives a much higher X-ray photon flux than the second segment 172. The first segment 170 or both the first segment 170 and the second segment 172 can give an accurate signal at low X-ray flux, while the second segment 172 can still give a signal proportional to the X-ray flux even at high X-ray flux (which would saturate the first segment 170), assuming that the maximum signal is limited by the readout electronics. The dimensions of the first segment 170 and the second segment 172 may vary in the direction 164 to alter the photon flux received by each segment 170, 172. A ratio of the length 174 to the length 176 may vary from 100:1 to 50:50. Besides significantly reducing power requirement of an imaging detector (e.g., CT imaging detector), the interlocked triangular pattern may enable larger z-coverage.

A large proportion of energy is required for a first amplifier (i.e., for each individual pixel) of a photon-counting detector. It is therefore desirable to reduce the number pixels to reduce the overall energy, while still enabling detection of the exact position. While charge sharing of a single pixel between multiple electrodes can add information about the spatial location of the interaction, it requires each sub-pixel electrode to count at the same rate as a "full pixel" electrode. Increasing the pixel size may reduce the overall count rate. Embodiments disclosed in FIGS. 15-18 make it possible through a pattern of the sub-pixel electrodes to simultaneously provide charge sharing characteristics (i.e., two-dimensional (2D) charge sharing) that change as function of both a first direction 178 (e.g., x-direction) and a second direction 180 (e.g., y-direction). The directions 178, 180 are both orthogonal to a path of X-ray photons. The sub-pixel electrodes have structures that are smaller than the size of a charge cloud. The pixels (e.g., electrode pixels such as anode pixels) in FIGS. 15-18 are disposed on one surface of a detection material (e.g., CZT, CdTe, or other suitable direct-conversion detector material) that generates signal in response to X-rays without a scintillator intermediary component. A common electrode may be disposed on the opposite side of the detection material. In certain embodiments, besides being associated with photon-counting detectors, the pixel arrangements in FIGS. 15-18 may be associated with phase-contrast imaging detectors.

Figure 15:
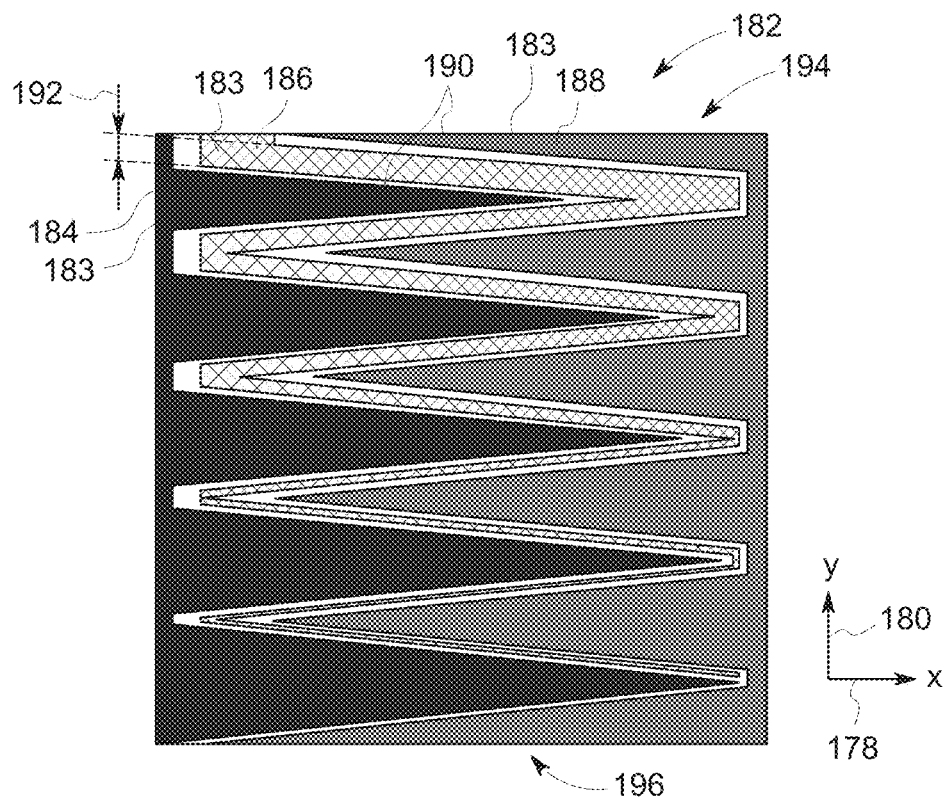
FIG. 15 depicts an electrode pixel having multiple sub-pixel electrodes, in accordance with aspects of the present disclosure.

FIG. 15 depicts an electrode pixel 182 having multiple sub-pixel electrodes. As depicted, the electrode pixel 182 includes three sub-pixel electrodes 183 (sub-pixel electrode 184, sub-pixel electrode 186, and sub-pixel electrode 188). The sub-pixel electrodes 183 are continuous electrodes. The sub-pixel electrodes 183 enable measuring three parameters (overall charge, location in the direction 178, and location in the direction 180). The sub-pixel electrodes include structural features or features (e.g., tapered portions 190) smaller than a size of a charge cloud and share the total charge for the electrode pixel 182. The sub-pixel electrodes 184 and 188 include tapered portions 190 that taper in the direction 178. The tapered portions 190 of the sub-pixel electrodes 184 and 188 form an interlocked triangular pattern. The sub-pixel electrode 186 is disposed between the sub-pixel electrodes 184 and 188 within this interlocked triangular pattern. As depicted in FIG. 15, the sub-pixel electrode 186 decreases in width 192 from end 194 to end 196 of the electrode pixel 182. As depicted in FIG. 15, the sub-pixel electrode 186 ceases along the interface between the sub-pixel electrodes 184 and 188 before reaching the end 196.

Figure 16:
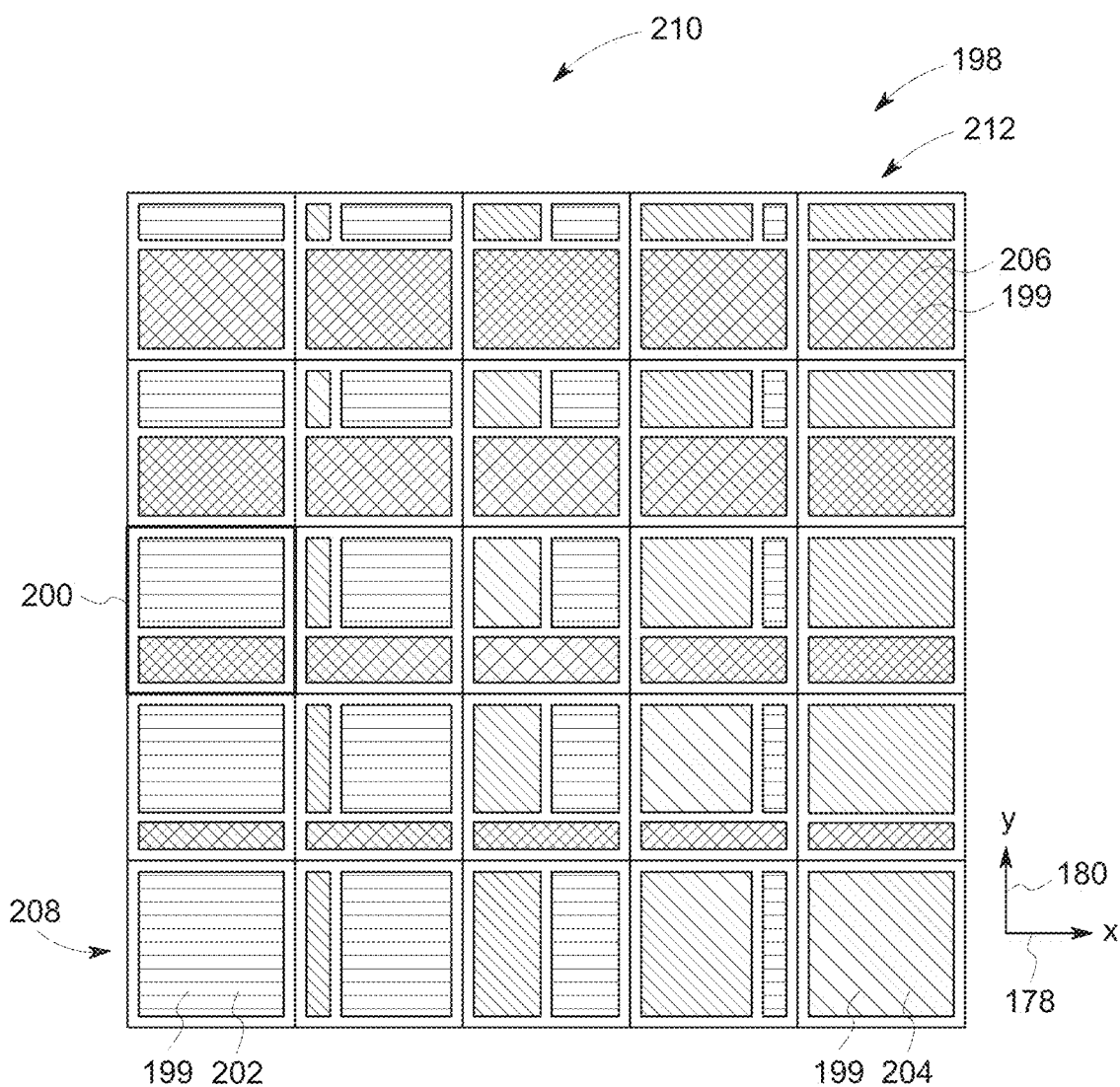
FIG. 16 depicts an electrode pixel having multiple pixelated electrodes (e.g., three pixelated electrodes), in accordance with aspects of the present disclosure.
Figure 17:
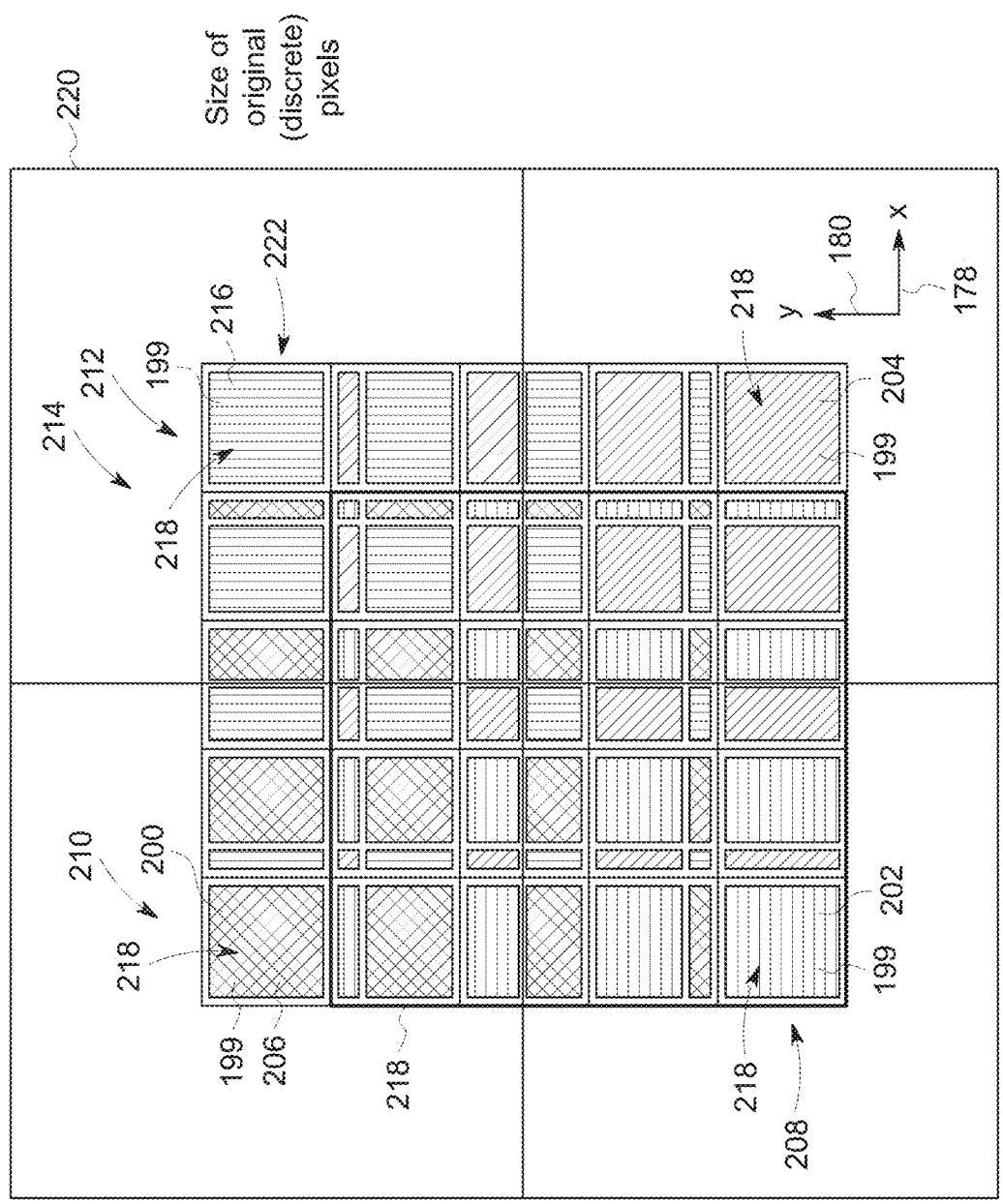
FIG. 17 depicts an electrode pixel having multiple pixelated electrodes (e.g., four pixelated electrodes), in accordance with aspects of the present disclosure.
Figure 18:
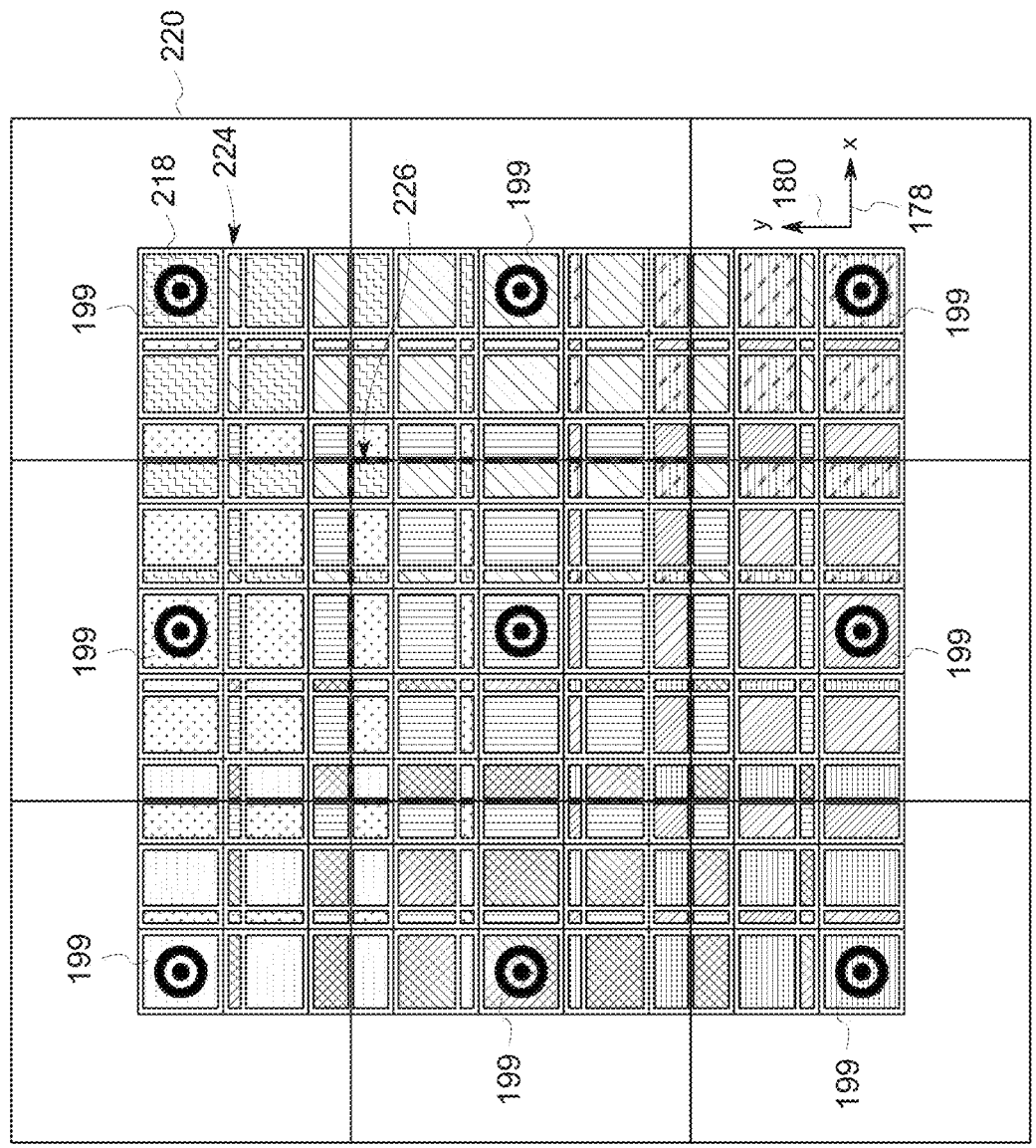
FIG. 18 depicts a number of adjacent electrode pixels having multiple pixelated electrodes, in accordance with aspects of the present disclosure.

As depicted in FIGS. 16-18, a better charge sharing may be achieved with small charge clouds by utilizing pixelated electrodes (as opposed to continuous electrodes). This controlled charge sharing in FIGS. 16-18 may improve resolution of an imaging detector (e.g., photon-counting detector for SPECT) while increasing pixel size and pixel pitch. FIG. 16 depicts an electrode pixel 198 having multiple pixelated electrodes 199. The electrode pixel 198 includes multiple sub-pixels 200 arranged in a square pattern. Each sub-pixel 200 is about the size of an electron cloud. It should be noted that the lines indicating the sub-pixels 200 are for visualization only and do not have a physical equivalent. The electrode pixel 198 includes three pixelated electrodes 199 (e.g., pixelated electrode 202, pixelated electrode 204, and pixelated electrode 206). Each sub-pixel 200 includes a portion of at least one of the pixelated electrodes 199. Some of the sub-pixels 200 include a portion of at least two of the pixelated electrodes 199. Some of the sub-pixels 200 include a portion of all three pixelated electrodes 199.

As depicted in a row 208 of sub-pixels 200, the ratio of an area of the pixelated electrode 202 to an area of the pixelated electrode 204 varies. For example, along the direction 178 going from right to left along the row 208, the ratio of the area of the pixelated electrode 202 to the area of the pixelated electrode 204 decreases and vice versa in the opposite direction. As depicted in a column 210 of sub-pixels 200, the ratio of an area of the pixelated electrode 202 to an area of the pixelated electrode 206 varies. For example, along the direction 180 going from bottom to top along the column 210, the ratio of the area of the pixelated electrode 202 to the area of the pixelated electrode 206 decreases and vice versa in the opposite direction. As depicted in a column 212 of sub-pixels 200, the ratio of an area of the pixelated electrode 204 to an area of the pixelated electrode 206 varies. For example, along the direction 180 going from bottom to top along the column 212, the ratio of an area of the pixelated electrode 204 to the area of the pixelated electrode 206 decreases and vice versa in the opposite direction. The changing pattern of the pixelated electrode 202 and the pixelated electrode 204 ensures charge splitting in the direction 178. The pixelated electrode 206 ensures continuously-changing charge sharing in the direction 180.

FIG. 17 depicts an electrode pixel 214 having multiple pixelated electrodes 199. The electrode pixel 214 includes multiple sub-pixels 200 arranged in a square pattern. Each sub-pixel 200 is about the size of an electron cloud. It should be noted that the lines indicating the sub-pixels 200 are for visualization only and do not have a physical equivalent.

The electrode pixel 214 includes four pixelated electrodes 199 (e.g., pixelated electrode 202, pixelated electrode 204, pixelated electrode 206, and pixelated electrode 216). The electrode pixel 214 is larger than the outline of the pixel building block (indicated by square 219) utilized in FIG. 16. By having four pixelated electrodes 199, more controlled charge is added in the area in-between centers 218 of pixels (e.g., discrete pixels that would be seen in a typical detector having a same of number square pixels) (outlined by squares 220). As depicted in FIG. 17, the electrode pixel 214 is larger than the standard pixel 220. Each sub-pixel 200 includes a portion of at least one of the pixelated electrodes 199. Some of the sub-pixels 200 include a portion of at least two of the pixelated electrodes 199. Some of the sub-pixels 200 include a portion of at least three pixelated electrodes 199. Some of the sub-pixels 200 include a portion of all four pixelated electrodes 199.

As depicted in a row 208 of sub-pixels 200, the ratio of an area of the pixelated electrode 202 to an area of the pixelated electrode 204 varies. For example, along the direction 178 going from right to left along the row 208, the ratio of the area of the pixelated electrode 202 to the area of the pixelated electrode 204 decreases and vice versa in the opposite direction. As depicted in a column 210 of sub-pixels 200, the ratio of an area of the pixelated electrode 202 to an area of the pixelated electrode 206 varies. For example, along the direction 180 going from bottom to top along the column 210, the ratio of the area of the pixelated electrode 202 to the area of the pixelated electrode 206 decreases and vice versa in the opposite direction. As depicted in a column 212 of sub-pixels 200, the ratio of an area of the pixelated electrode 204 to an area of the pixelated electrode 216 varies. For example, along the direction 180 going from bottom to top along the column 212, the ratio of an area of the pixelated electrode 204 to the area of the pixelated electrode 216 decreases and vice versa in the opposite direction. As depicted in a row 222 of sub-pixels 200, the ratio of an area of the pixelated electrode 206 to an area of the pixelated electrode 216 varies. For example, along the direction 178 going from left to right along the row 222, the ratio of an area of the pixelated electrode 206 to the area of the pixelated electrode 216 decreases and vice versa in the opposite direction.

FIG. 18 depicts a number of adjacent electrode pixels 224 (or portions of the electrode pixels 224) having multiple pixelated electrodes 199. Each electrode pixel 224 includes four pixelated electrodes 199 as described in FIG. 17. A central (e.g., distributed) electrode pixel 226 includes pixelated electrodes 199 that extend into all of the neighboring electrode pixels 224 (8 total neighboring electrode pixels 224), while pixelated electrodes 199 of the neighboring electrode pixels 224 extend into the central electrode pixel 226. Centers 218 of the pixels 220 are indicated by a bullseye (which is for visualization purposes and does not have a physical equivalent). The utilization of pixel building blocks having multiple pixelated electrodes provides more robustness to high count rates. For example, two coincident events will still be attributed to both a correct pixel and a correct location within a pixel.

Technical effects of the disclosed embodiments include providing X-ray detectors having a reduced number of pixels and a reduction in the energy required for readout. Despite the pixel reduction, the spatial resolution of the X-ray detectors are maintained or improved. Indeed, the spatial resolution may be better than the pixel pitch. For example in CT detectors, detector heating may be reduced while enabling larger detector coverage. For example, in a low count rate application such as with a SPECT detectors, spatial resolution may be improved and/or pixel pitch increased.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

This written description uses examples to disclose the present subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A phase-contrast imaging detector, comprising:
   a plurality of pixels, each pixel comprising:
      a detection material that generates a measurable parameter in response to X-ray photons; and
      a plurality of sub-pixel resolution readout structures, wherein the sub-pixel resolution readout structures are in an alternating pattern with a spacing therebetween that is larger than a frequency of a phase-contrast interference pattern but small enough to enable charge sharing between adjacent sub-pixel resolution readout structures when an X-ray photon hits between the adjacent sub-pixel resolution readout structures;
   readout circuitry configured to read out signals from the plurality of sub-pixel readout structures;
   wherein the plurality of sub-pixel resolution readout structures comprises two or more electrodes having alternating arms that form an interleaved comb structure.

2. The phase-contrast imaging detector of claim 1, wherein the spacing is larger than the frequency of the phase-contrast interference pattern by an integer multiple.

3. The phase-contrast imaging detector of claim 1, wherein a width of each alternating arm is less than the spacing.

4. The phase-contrast imaging detector of claim 1, wherein two or more electrodes run parallel to a path of the of X-ray photons.

5. The phase-contrast imaging detector of claim 1, comprising a switch coupled to the readout circuitry, wherein the switch is configured to enable selective read out of signals from the two or more electrodes to selectively associate each of the two or more electrodes with a different phase of the phase-contrast interference pattern.

6. The phase-contrast imaging detector of claim 1, wherein the alternating arms are spaced at 5 to 50 micrometers from each other.

7. The phase-contrast imaging detector of claim 1, wherein each electrode of the two or more electrodes is shaped so that adjacent electrodes form an interlocked triangular pattern between themselves to enable charge sharing, and wherein the adjacent electrodes overlap in a direction.

8. The phase-contrasting imaging detector of claim 7, wherein the direction is parallel to a path of the X-ray photons.

9. The phase-contrast imaging detector of claim 7, wherein each electrode of the two or more electrodes comprises a first segment physically separate from a second segment in a co-linear arrangement along the direction.

10. The phase-contrast imaging detector of claim 9, wherein the first segment is longer than the second segment in the direction.

11. The phase-contrast imaging detector of claim 10, wherein the first segment is configured to encounter X-ray photons before the second segment.

12. The phase-contrast imaging detector of claim 10, wherein the second segment is configured to enable accurate measurement of the X-ray photons in the presence of an X-ray photon flux that saturates the first segment.

13. The phase-contrast imaging detector of claim 9, wherein the interlocked triangular pattern is configured to define the charge sharing between the adjacent electrodes so that a charge in each adjacent electrode is a linear function of location between centers of the adjacent pixels.

14. An imaging detector, comprising:
a plurality of pixels, each pixel comprising:
a detection material that generates a measurable parameter in response to X-ray photons; and
a plurality of sub-pixel resolution readout structures, wherein the sub-pixel resolution readout structures are in an alternating pattern with a spacing therebetween that is larger than a frequency of a phase-contrast interference pattern but small enough to enable charge sharing between adjacent sub-pixel resolution readout structures when an X-ray photon hits between the adjacent sub-pixel resolution readout structures;
readout circuitry configured to read out signals from the plurality of sub-pixel readout structures;
wherein the plurality of sub-pixel resolution readout structures comprises two or more electrodes having alternating arms that form an interleaved comb structure; and
wherein each electrode of the two or more electrodes is shaped so that adjacent electrodes form an interlocked triangular pattern between themselves to enable charge sharing, and wherein the adjacent electrodes overlap in a direction parallel to a path of the X-ray photons, and wherein each electrode of the two or more electrodes comprises a first segment physically separate from a second segment in a co-linear arrangement along the direction, the second segment being configured to enable accurate measurement of the X-ray photons in the presence of an X-ray photon flux that saturates the first segment.

* * * * *